(12) United States Patent
Fakhrzadeh et al.

(10) Patent No.: US 11,406,478 B2
(45) Date of Patent: *Aug. 9, 2022

(54) METHODS FOR CUSTOMIZED DENTAL IMPLANTS FORMED OF A BIOMETRIC COMPOSITE MATERIAL AND METHODS OF MANUFACTURE THEREOF

(71) Applicant: Rutgers, The State University of New Jersey, New Brunswick, NJ (US)

(72) Inventors: Amir Fakhrzadeh, East Brunswick, NJ (US); Mohammad Ali Saghiri, Hackensack, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 156 days.

This patent is subject to a terminal disclaimer.

(21) Appl. No.: 16/791,090

(22) Filed: Feb. 14, 2020

(65) Prior Publication Data
US 2020/0179085 A1 Jun. 11, 2020

Related U.S. Application Data

(63) Continuation-in-part of application No. 16/790,202, filed on Feb. 13, 2020, and a continuation-in-part of
(Continued)

(51) Int. Cl.
*A61C 8/00* (2006.01)
*A61L 27/10* (2006.01)
(Continued)

(52) U.S. Cl.
CPC .......... *A61C 8/0012* (2013.01); *A61C 8/0036* (2013.01); *A61C 13/0004* (2013.01);
(Continued)

(58) Field of Classification Search
CPC ..... A61C 8/0012; A61C 8/0036; A61L 27/10; A61L 27/12; A61L 27/56; A61L 27/3604;
(Continued)

(56) References Cited

U.S. PATENT DOCUMENTS

| 4,051,598 A | 10/1977 | Sneer | |
|---|---|---|---|
| 8,470,308 B2 * | 6/2013 | Wasielewski | ........ A61K 9/0009 424/93.1 |

(Continued)

OTHER PUBLICATIONS

International Search Report and Written Opinion dated Nov. 1, 2018, issued by the U.S. Patent and Trademark Office in international application No. PCT/US2018/046515.
(Continued)

*Primary Examiner* — C Melissa Koslow
(74) *Attorney, Agent, or Firm* — Greenberg Traurig, LLP

(57) ABSTRACT

A biomimetic composite material includes a bioactive cement material, an autologous dentin matrix, and an inorganic nano-reinforcement material. A dental implant includes a body including a biomimetic composite material, wherein the biomimetic composite material includes a bioactive cement material, an autologous dentin matrix, and an inorganic nano-reinforcement material.

15 Claims, 17 Drawing Sheets

Related U.S. Application Data application No. PCT/US2018/046515, filed on Aug. 13, 2018.

(60) Provisional application No. 62/946,394, filed on Dec. 10, 2019, provisional application No. 62/545,113, filed on Aug. 14, 2017.

(51) Int. Cl.

| | |
|---|---|
| *A61L 27/56* | (2006.01) |
| *A61L 27/12* | (2006.01) |
| *A61L 27/06* | (2006.01) |
| *A61C 13/08* | (2006.01) |
| *A61C 13/00* | (2006.01) |
| *A61L 27/36* | (2006.01) |
| *A61K 6/851* | (2020.01) |
| *A61K 6/80* | (2020.01) |
| *A61K 6/849* | (2020.01) |
| *A61K 6/853* | (2020.01) |
| *B33Y 80/00* | (2015.01) |

(52) U.S. Cl.
CPC ........ *A61C 13/0019* (2013.01); *A61C 13/081* (2013.01); *A61K 6/80* (2020.01); *A61K 6/849* (2020.01); *A61K 6/851* (2020.01); *A61K 6/853* (2020.01); *A61L 27/06* (2013.01); *A61L 27/10* (2013.01); *A61L 27/12* (2013.01); *A61L 27/3604* (2013.01); *A61L 27/56* (2013.01); *B33Y 80/00* (2014.12)

(58) Field of Classification Search
CPC ........ A61K 6/849; A61K 6/851; A61K 6/853; A61K 6/80
See application file for complete search history.

(56) References Cited

U.S. PATENT DOCUMENTS

| | | | |
|---|---|---|---|
| 2008/0090207 A1* | 4/2008 | Rubbert | ............... A61C 8/0036 433/171 |
| 2010/0086618 A1 | 4/2010 | Pashlet et al. | |
| 2010/0215617 A1 | 8/2010 | Wasielewski | |
| 2012/0156308 A1 | 6/2012 | Lovschall et al. | |
| 2013/0143179 A1 | 6/2013 | Um | |

OTHER PUBLICATIONS

European Search Report for EP Application No. 18846032.3, dated Mar. 24, 2021, 8 pages.

Gurtu et al., "Evaluation of effect of dentin powder on antibacterial properties of Mineral Trioxide Aggregate—An in vitro study", Minerva Stomatologica, Jun. 2014, pp. 120-127, vol. 26, Issue 1, Italy.

Graftys, "Grafty's Products", Oct. 8, 2018, <https://www.graftys.com/injectable-ceramic-products/>, 6 pages, France and United States.

Hilley et al., "Bioceramics in Endodontics", Clinical Update, Navel Postgraduate Dental School, Published in 2013, 2 pages, vol. 35, No. 4, Bethesda, Maryland.

Yakoob et al., "Evaluate the use of fresh Autogenous cement and dentine as bone graft to repair bone defects in dogs: experimental study", International Dental Journal of Student Research, Jun. 30, 2016, pp. 97-100, vol. 4, Issue 2, United States.

* cited by examiner

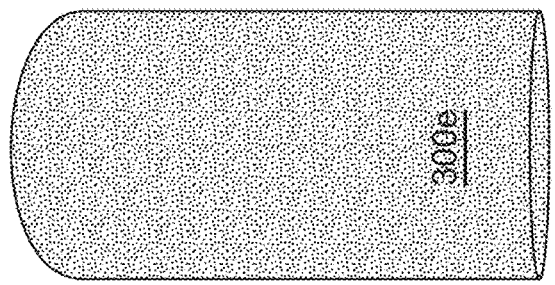
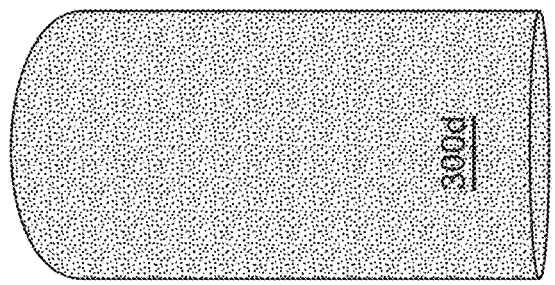
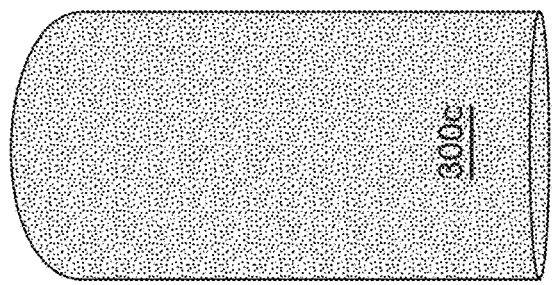
FIG. 3

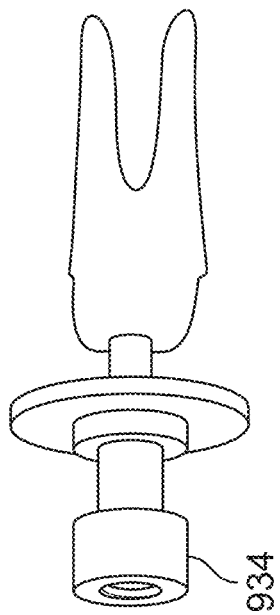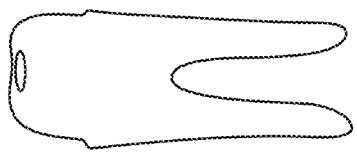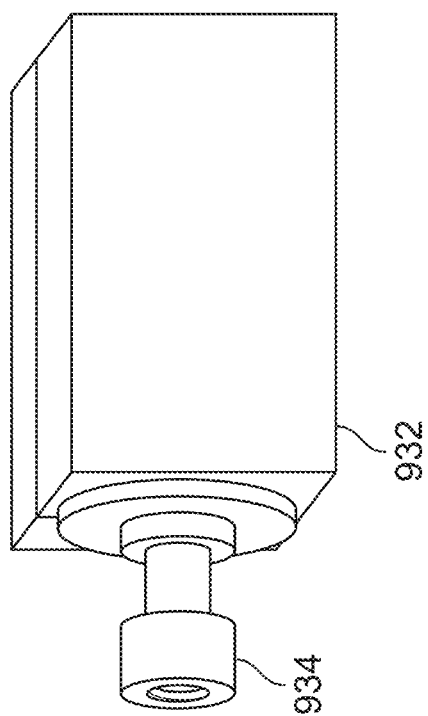

METHODS FOR CUSTOMIZED DENTAL IMPLANTS FORMED OF A BIOMETRIC COMPOSITE MATERIAL AND METHODS OF MANUFACTURE THEREOF

CROSS-REFERENCE TO RELATED APPLICATIONS

The present application is a continuation-in-part application that claims priority to and the benefit of PCT Application No. PCT/US2018/046515, filed on Aug. 13, 2018, which claims priority to and the benefit of U.S. Provisional Patent Application Ser. No. 62/545,113, filed Aug. 14, 2017, the disclosure of each of which is hereby expressly incorporated by reference in its entirety. The present application further claims priority to and the benefit of co-pending U.S. application Ser. No. 16/790,202, filed Feb. 13, 2020, which in turn claims priority to and the benefit of U.S. Provisional Patent Application Ser. No. 62/946,394, filed Dec. 10, 2019, the disclosure of each of which is hereby expressly incorporated by reference in its entirety.

TECHNICAL FIELD

The present invention relates to the field of dentistry and more particularly, relates to customized dental implants that are formed of an injectable biomimetic composite material that is for the application of immediate tooth replacement.

BACKGROUND OF THE INVENTION

Titanium screw type dental implants are the current standard for replacing failing or missing natural teeth that require replacement due to tooth decay, periodontal disease, or trauma. The conventional process for placing standard dental implant involves a process where a hole is drilled into the bone and the implant device, typically made of titanium alloy (or other metal or ceramic material), is inserted (or threaded) into the cavity and allowed to fuse with the bone by a process known as osseointegration.

SUMMARY OF THE INVENTION

In accordance with some embodiments, the present disclosure is directed to a dental implant including a body formed of a biomimetic composite material that includes processed dentin from an extracted tooth and a bioactive cement.

In some embodiments, the processed dentin comprises dentin particles.

In some embodiments, the bioactive cement comprises a calcium silicate based dental cement.

In some embodiments, the body is formed entirely of the biomimetic composite material.

In some embodiments, the body comprises a core and an outer surface layer that is disposed over at least a portion of the core, the core and the outer surface layer being formed of different materials.

In some embodiments, the core is formed at least substantially of the bioactive cement and the outer surface layer is formed of the biomimetic composite material.

In some embodiments, a thickness of the outer surface layer is between about 500 microns and about 1500 microns.

In some embodiments, the outer surface layer covers at least substantially all of the core.

In some embodiments, the dentin comprises from about 10 percent to about 50 percent by weight of the total biomimetic composite material.

In some embodiments, the biomimetic composite material comprises dentin particles mixed with the bioactive cement in powder form.

In some embodiments, the dentin particles have a particle size between about 50 microns and about 1500 microns.

In some embodiments, the dentin comprises a plurality of dentin particles with each particle have a multitude of exposed dentinal tubules, the biomimetic composite material being defined by micro-mechanical bonding of the bioactive cement to the dentin particles as a result of flow of the bioactive cement into the dentinal tubules.

In some embodiments, a final shape and size of the body are selected in view of an image of the tooth that is extracted and mimics the shape and size of the extracted tooth.

In some embodiments, the bioactive cement comprises a dental cement selected from the group consisting of: a calcium silicate-based cement, a mineral trioxide aggregate (MTA), and a glass ionomer cement.

In accordance with some embodiments, the present disclosure is directed to a method for fabricating a dental implant including the steps of: imaging a patient's dental structures including at least one tooth for removal; processing an extracted tooth from a person so as to generate dentin particles; and fabricating the dental implant based on the imaging, the dental implant comprising a body formed of a biomimetic composite material that includes the processed dentin particles and a bioactive cement.

In some embodiments, the bioactive cement comprises a calcium silicate based dental cement.

In some embodiments, the body is formed entirely of the biomimetic composite material.

In some embodiments, the body comprises a core and an outer surface layer that is disposed over at least a portion of the core, the core and the outer surface layer being formed of different materials.

In some embodiments, the core is formed at least substantially of the bioactive cement and the outer surface layer is formed of the biomimetic composite material.

In some embodiments, a thickness of the outer surface layer is between about 500 microns and about 1500 microns.

In some embodiments, the outer surface layer covers at least substantially all of the core.

In some embodiments, the dentin comprises from about 10 percent to about 50 percent by weight of the total biomimetic composite material.

In some embodiments, the step of fabricating the dental implant comprises casting the biomimetic composite material in a mold to form the body.

In some embodiments, the mold is fabricated based on additive manufacturing.

In some embodiments, the mold is fabricated by embedding the extracted tooth into an impressionable material to form two mold halves when the extracted tooth is removed.

In some embodiments, the method further includes the step of milling the cast body to form the dental implant.

In some embodiments, the extracted tooth is from the patient's mouth.

In accordance with some embodiments, the present disclosure is directed to dental treatment method including the steps of: imaging a patient's dental structures including a tooth for removal; processing an extracted tooth so as to generate dentin particles; fabricating a dental implant based on the imaging, the dental implant comprising a body formed of a biomimetic composite material that includes the processed dentin particles and a bioactive cement; and implanting the dental implant at a surgical site.

In some embodiments, the method further includes the step of extracting the tooth from the surgical site of the patient.

In some embodiments, all of the steps are performed in one patient sitting and the dental implant is implanted immediately after extraction of the tooth and creation of the implant.

In accordance with some embodiments, the present disclosure is directed to a dental implant including: a hollow tooth shell formed from a patient's tooth and defined at least by a dentin layer with a hollow interior defined therein; and a core that is disposed within the hollow interior of the tooth shell and is formed of a bioactive cement that flows into the dentinal tubules to generate a composite dentin/cement zone around the core.

In some embodiments, the hollow tooth shell is further defined by an outer enamel layer that covers at least a portion of the dentin layer.

In some embodiments, the hollow tooth shell is open along it top coronal surface to allow formation of the core by addition of the cement to the hollow interior through the opening along the top coronal surface.

In accordance with some embodiments, the present disclosure is directed to a biomimetic composite material including a bioactive cement material; an autologous dentin matrix; and an inorganic nano-reinforcement material.

In some embodiments, the bioactive cement material comprises a calcium silicate based dental cement.

In some embodiments the autologous dentin matrix comprises dentin particles.

In some embodiments, the inorganic nano-reinforcement material comprises titanium.

In some embodiments, the inorganic nano-reinforcement material comprises $TI_6AL_4V$.

In some embodiments, the inorganic nano-reinforcement material is in the form of a foam.

In some embodiments, the inorganic nano-reinforcement material is in the form of particles.

In some embodiments, the autologous dentin matrix comprises from 10 percent to 20 percent by weight of the biomimetic composite material.

In some embodiments, the inorganic nano-reinforcement material comprises from 10 percent to 35 percent by weight of the biomimetic composite material.

In some embodiments, the ratio of bioactive cement material to autologous dentin matrix to reinforcement material is 1:1:3.

In some embodiments, the autologous dentin matrix comprises dentin particles with a particle size of 150 microns to 200 microns.

In some embodiments, the bioactive cement material comprises a mineral trioxide aggregate.

In accordance with some embodiments, the present disclosure is directed to a dental implant including a body including a biomimetic composite material, wherein the biomimetic composite material includes: 1) a bioactive cement material; 2) an autologous dentin matrix; and 3) an inorganic nano-reinforcement material.

In some embodiments, the bioactive cement material comprises a calcium silicate based dental cement.

In some embodiments, the inorganic nano-reinforcement material comprises titanium.

In some embodiments, the inorganic nano-reinforcement material is in the form of a foam.

In some embodiments, the inorganic nano-reinforcement material is in the form of particles.

In some embodiments, the autologous dentin matrix comprises dentin particles.

In some embodiments, the autologous dentin matrix comprises from 10 percent to 20 percent by weight of the biomimetic composite material.

In some embodiments, the inorganic nano-reinforcement material comprises from 10 percent to 35 percent by weight of the biomimetic composite material.

In some embodiments, the autologous dentin matrix comprises dentin particles with a particle size of 150 microns to 200 microns.

In some embodiments, the ratio of bioactive cement material to autologous dentin matrix to reinforcement material is 1:1:3.

BRIEF DESCRIPTION OF THE DRAWINGS

FIG. 3 is a cross-sectional view of four exemplary titanium foams according to exemplary embodiments of the present disclosure;

FIG. 15A-15C illustrate the steps for forming composite blocks that are subjected to a milling operation to form the customized tooth form implant according to exemplary embodiments of the present disclosure;

DETAILED DESCRIPTION OF THE INVENTION

Figure 1:
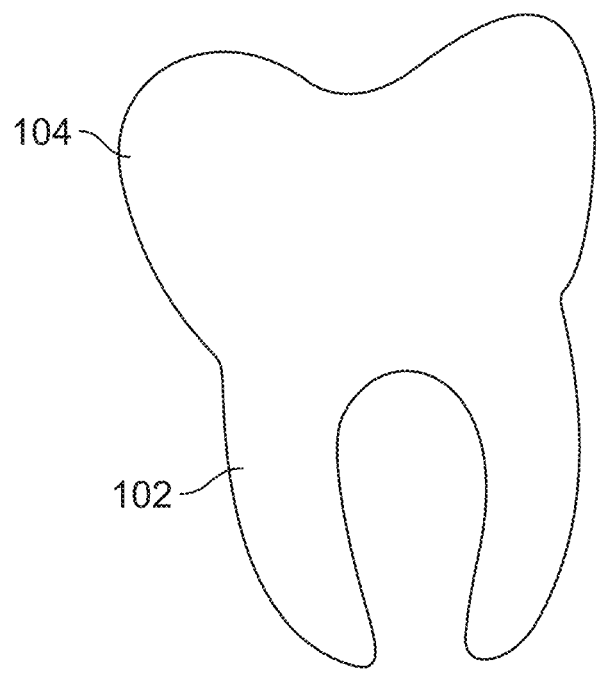
FIG. 1 is a cross-sectional view of an exemplary tooth.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

For the following defined terms, these definitions shall be applied, unless a different definition is given in the claims or elsewhere in this specification.

As used herein, the term "proximal" is defined as a direction toward a user and the term "distal" is defined as a direction away from a user As used herein, the singular forms "a", "an", and "the" include plural referents unless the content clearly dictates otherwise. As used in this specification and the appended claims, the term "or" is generally employed in its sense including "and/or" unless the content clearly dictates otherwise.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

Although some suitable dimensions ranges and/or values pertaining to various components, features and/or specifications are disclosed, one of skill in the art, incited by the present disclosure, would understand desired dimensions, ranges and/or values may deviate from those expressly disclosed.

While dental implants are the current state of the art for tooth replacement, they involve an invasive surgical procedure and significant risks. Aside from intraoperative surgical risks, a high incidence of titanium implant failures is reported after placement due to a variety of reasons.

Often, when an implant fails, the amount of bone already lost or that needs to be removed in order to retrieve the titanium implant can be catastrophic and this makes replacing that implant extremely difficult, if not impossible. This bone loss leaves many patients debilitated and often times requires more extensive surgeries to compensate for the damage.

A major problem with these implants is that they are all a variation of the same screw type design and come in slightly different lengths, diameters, and surface modifications. In clinical practice, the occurrence of these variations translates to adjusting the patient to fit the needs of the implant rather than modifying the device to fit the needs of the patient.

The present disclosure relates to a novel biomimetic composite material for casting into dental implant molds or direct injection into fresh extraction sockets to create customizable dental implants for tooth replacement. In some embodiments, the biomimetic composite material includes a bioactive cement material, an autologous dentin matrix, and an inorganic nano-reinforcement filler. In some embodiments, the composition and geometry of the autologous dentin matrix and the inorganic nano-reinforcement filler is modified in order to increase the release of inorganic trace elements including Calcium and Strontium, as well as to improve the biological and mechanical properties of the biomimetic composite material.

As depicted in FIG. 1, the tooth is divided into two parts: (1) the root 102, which extends below the gum line and anchors the tooth into the bone; and (2) the crown 104, which is the visible, white part of the tooth. A human tooth includes four types of tissue, each performing a different function.

The first type of tooth tissue is enamel. Enamel is the visible substance that covers the crown of the tooth. Harder than bone, enamel protects the tooth from decay. Enamel is made up of phosphorous and calcium in a hydroxyapatite form, which is more mineralized than dentin and bone. They high hydroxyapatite content in enamel and natural teeth imparts strength and resistance to wear or breakdown.

The second type of tooth tissue is dentin. Dentin is the calcified layer just beneath the enamel. Dentin is also composed of calcium and phosphate and is harder than bone, but not as hard as enamel. Dentin makes up the majority of the crown and the roots of a tooth and is very similar in chemical composition to bone, except that it has a slightly higher mineral content. Dentin, like enamel, is composed of an organic (primarily collagen) matrix and an inorganic hydroxyapatite (calcium and phosphorous) component.

The third type of tooth tissue is cementum. Cementum covers the root dentin on one side and the periodontal ligament, which is attached to the surrounding alveolar bone, on the other side. There are two types of cementum: cellular and acellular. In some cases, cementum can be lost from the tooth in areas with disease or after mechanical debridement (e.g., by aggressive tooth brushing or from instrumentation at the dental office). Cementum does have the capacity at times to reform around the tooth after it has been lost, assuming that there is ample blood supply and that cementoblasts (cementum producing cells) are still present within the periodontal ligament space. The cementum, periodontal ligament and alveolar bone make up what is known as the Periodontium. The Periodontium retains teeth within the jawbone and is only present around natural teeth.

The fourth type of tooth tissue is pulp. Pulp is located at the center of the tooth and contains blood vessels, nerves and other soft tissues that deliver nutrients and signals to the tooth.

There are four types of teeth, each of which performs its own function. Incisors are the eight teeth in the front and center of the mouth (four on top and four on the bottom) that are designed to tear food apart in order to be chewed by the back teeth. Canines are the four sharpest teeth and are also used for ripping and tearing food apart. Premolars, or bicuspids, are used for chewing and grinding food. There are four premolars on each side of the mouth—two upper and two lower. Molars are the teeth found furthest back on both sides of the mouth. Molars are used for chewing and grinding food and often have multiple roots to withstand the highest chewing forces in the oral cavity. Each type of tooth also has its own shape. Thus, extraction sockets and tooth form implants are dictated by the type of tooth that is to be replaced.

In some embodiments, the present disclosure relates to a biomimetic composite material including a bioactive cement material and an autologous dentin matrix that can be used to fill patient-specific extraction sockets and to form custom patient-specific tooth molds.

In some embodiments, the bioactive cement material includes a cement that is a mineral trioxide aggregate (MTA) that is mixed with water, calcium hydroxide (CH) and calcium silicate hydrate to form a calcium silicate cement (CSC). Calcium silicate cement releases calcium ions for cell attachment and proliferation, creates an antibacterial environment by its alkaline pH, and modulates cytokine production. In some embodiments, the bioactive cement material releases calcium to promote osteointegration. In some embodiments, the bioactive cement is Biodentine®, a CSC commercially available from Septodont. The mechanical properties of Biodentine® have been tailored to mimic natural human dentine and the product is marketed as "Dentin Replacement Material" due to its nearly identical physicochemical properties.

In some embodiments, a dual cement matrix is formed by mixing the bioactive cement material (e.g., Biodentine® material) and the autologous dentin matrix. In some embodiments, the autologous dentin matrix is a processed dentin material. Inclusion of the autologous dentin matrix in the bioactive cement material allows the biomimetic material to more closely replicate the properties of natural dentin. In some embodiments, the dentin material is from an extracted tooth from the patient, another human, or an animal donor/cadaver. In some embodiments, the dentin is from primary teeth (baby teeth) or permanent (wisdom teeth/premolars extracted for orthodontic purposes) teeth. Details of the processing of the dentin material are described below.

In some embodiments, the particle orientation and shape is variable. In some embodiments, the dentin particles may be flakelike, spherical or wedge shaped. In some embodiments, the particles are wedge-shaped with varying surface topography.

In some embodiments, the dentin particles have a particle size of 150 microns to 200 microns. In other embodiments, the dentin particles have a particle size of 160 microns to 200 microns. In other embodiments, the dentin particles have a particle size of 170 microns to 200 microns. In other embodiments, the dentin particles have a particle size of 180 microns to 200 microns. In other embodiments, the dentin particles have a particle size of 190 microns to 200 microns.

In some embodiments, the dentin particles have a particle size of 150 microns to 190 microns. In other embodiments, the dentin particles have a particle size of 150 microns to 180 microns. In other embodiments, the dentin particles have a particle size of 150 microns to 170 microns. In other embodiments, the dentin particles have a particle size of 150 microns to 160 microns.

In some embodiments, the dentin particles have a particle size of 160 microns to 190 microns. In other embodiments, the dentin particles have a particle size of 170 microns to 190 microns. In other embodiments, the dentin particles have a particle size of 180 microns to 190 microns. In other embodiments, the dentin particles have a particle size of 160 microns to 180 microns. In other embodiments, the dentin particles have a particle size of 170 microns to 180 microns. In other embodiments, the dentin particles have a particle size of 160 microns to 170 microns.

Once processed, the dentin particles taken from the tooth can be stored under dry conditions for use for the same patient. The dentin particulate can be stored in the office or in an offsite facility. More specifically, the dentin can be stored in: 1) either vacuum-sealed dry conditions or a designated freezer for short-term to long term storage in the dental office; 2) an offsite facility using long-term storage protocols (Schwartz 1986, IJOMS) which can be modified to replace human serum and tissue culture media with phosphate buffered saline (PBS) or distilled water; and/or 3) storage chambers that are specifically designed to house teeth in a manner that reduces microbial contamination or degradation of the material and allows for safe and stable transport and long term storage of the extracted tooth material.

The dual cement matrix including the bioactive cement material and the autologous dentin matrix is, in some embodiments, set by a hydration reaction. For example, in an embodiment, a calcium silicate cement reacts via a hydration based reaction and creates a calcium-silicate-hydrate (C—S—H) gel. The C—S—H gel is the most abundant reaction product, occupying about 80% of the paste volume and is responsible for most of the bioactive properties of the dual cement matrix. The setting of the dual cement matrix results in an extremely alkaline environment that can reach up to a pH of 11. One key feature of the present biomimetic composite material is that, unlike other cement systems, the biomimetic composite material maintains its insolubility in these highly alkaline environments without compromising biocompatibility or mechanical properties.

In some embodiments, the ratio of the bioactive cement material to the autologous dentin matrix is [100:1]. In other embodiments, the ratio of the bioactive cement to dentin is [90:1]. In other embodiments, the ratio of the bioactive cement to dentin is [80:1]. In other embodiments, the ratio of the bioactive cement material to the autologous dentin is [70:1]. In other embodiments, the ratio of the bioactive cement material to the autologous dentin is [60:1]. In other embodiments, the ratio of the bioactive cement material to the autologous dentin is [50:1]. In other embodiments, the ratio of the bioactive cement material to the autologous dentin is [40:1].

In some embodiments, the present disclosure also relates to a biomimetic composite material including a bioactive cement material, an autologous dentin matrix, and an inorganic nano-reinforcement filler (reinforcement material) that is incorporated into the bioactive cement material.

The reinforcement material increases the compressive strength and improves the tensile strength of the bioactive cement material and the resulting biomimetic composite material. In some embodiments, the reinforcement material increases the mechanical properties of the biomimetic material from 50 Mpa to 800 Mpa. In other embodiments, the reinforcement material increases the mechanical properties of the biomimetic material from 100 Mpa to 800 Mpa. In other embodiments, the reinforcement material increases the mechanical properties of the biomimetic material from 200 Mpa to 800 Mpa. In other embodiments, the reinforcement material increases the mechanical properties of the biomimetic material from 300 Mpa to 800 Mpa. In other embodiments, the reinforcement material increases the mechanical properties of the biomimetic material from 400 Mpa to 800 Mpa. In other embodiments, the reinforcement material increases the mechanical properties of the biomimetic material from 500 Mpa to 800 Mpa. In other embodiments, the reinforcement material increases the mechanical properties of the biomimetic material from 600 Mpa to 800 Mpa. In other embodiments, the reinforcement material increases the mechanical properties of the biomimetic material from 700 Mpa to 800 Mpa.

In some embodiments, the reinforcement material increases the mechanical properties of the biomimetic material from 100 Mpa to 700 Mpa. In other embodiments, the reinforcement material increases the mechanical properties of the biomimetic material from 100 Mpa to 600 Mpa. In other embodiments, the reinforcement material increases the mechanical properties of the biomimetic material from 100 Mpa to 500 Mpa. In other embodiments, the reinforcement material increases the mechanical properties of the biomimetic material from 100 Mpa to 400 Mpa. In other embodiments, the reinforcement material increases the mechanical properties of the biomimetic material from 100 Mpa to 300 Mpa. In other embodiments, the reinforcement material increases the mechanical properties of the biomimetic material from 100 Mpa to 200 Mpa.

In some embodiments, the reinforcement material increases the mechanical properties of the biomimetic material from 200 Mpa to 700 Mpa. In other embodiments, the reinforcement material increases the mechanical properties of the biomimetic material from 300 Mpa to 600 Mpa. In other embodiments, the reinforcement material increases the mechanical properties of the biomimetic material from 400 Mpa to 500 Mpa. In other embodiments, the reinforcement material increases the mechanical properties of the biomimetic material from 500 Mpa to 700 Mpa. In other embodiments, the reinforcement material increases the mechanical properties of the biomimetic material from 300 Mpa to 600 Mpa. In other embodiments, the reinforcement material increases the mechanical properties of the biomimetic material from 200 Mpa to 400 Mpa.

In some embodiments, the reinforcement material is a bio-stable material that is stable during the hydration reaction of the dual cement matrix and after exposure to tissues and body fluid. The reinforcement material, in some embodiments, does not chemically react and agglomerate when in a solution and can easily and uniformly disperse during mixing and hydration. Another unique feature of the reinforcement material is the hydrophilicity thereof. Normally, metals and metal oxides are hydrophobic, which makes reproducibly obtaining a good mixture with the dual cement matrix challenging. In contrast, the present reinforcement material has increased wettability, as compared to other metals, and therefore is better suited for integration into the dual cement matrix during the hydration process. Additionally, the reinforcement material prevents the phenomena of stress shielding and stress concentration, two common causes of failure in conventional cements.

Exemplary reinforcement materials include, but are not limited to: titanium, titanium oxide, polypropylene, polystyrene, silk, or other materials.

In some embodiments, the reinforcement material is in the form of particles such as fibers, nano rods or needles.

In some embodiments, the particles are electrically charged and added to a fluid to prevent agglomeration thereof. In some embodiments, the particles have a length of 5 microns to 30 microns. In other embodiments, the particles have a length of 10 microns to 30 microns. In other embodiments, the particles have a length of 15 microns to 30 microns. In other embodiments, the particles have a length of 20 microns to 30 microns. In other embodiments, the particles have a length of 25 microns to 30 microns.

In some embodiments, the particles have a length of 5 microns to 25 microns. In other embodiments, the particles have a length of 5 microns to 20 microns. In other embodiments, the particles have a length of 5 microns to 15 microns. In other embodiments, the particles have a length of 5 microns to 10 microns.

In some embodiments, the particles have a length of 10 microns to 15 microns. In other embodiments, the particles have a length of 10 microns to 20 microns. In other embodiments, the particles have a length of 10 microns to 25 microns. In other embodiments, the particles have a length of 15 microns to 20 microns. In other embodiments, the particles have a length of 15 microns to 25 microns. In other embodiments, the particles have a length of 20 microns to 25 microns.

In some embodiments, the particles have a diameter of 1 micron to 10 microns. In other embodiments, the particles have a diameter of 2 microns to 10 microns. In other embodiments, the particles have a diameter of 4 microns to 10 microns. In other embodiments, the particles have a diameter of 6 microns to 10 microns. In other embodiments, the particles have a diameter of 8 microns to 10 microns.

In some embodiments, the particles have a diameter of 1 micron to 8 microns. In other embodiments, the particles have a diameter of 1 micron to 6 microns. In other embodiments, the particles have a diameter of 1 micron to 4 microns. In other embodiments, the particles have a diameter of 1 micron to 2 microns.

In some embodiments, the particles have a diameter of 2 microns to 8 microns. In other embodiments, the particles have a diameter of 6 microns to 8 microns. In other embodiments, the particles have a diameter of 4 microns to 6 microns. In other embodiments, the particles have a diameter of 2 microns to 4 microns. In other embodiments, the particles have a diameter of 4 microns to 8 microns.

Figure 2:
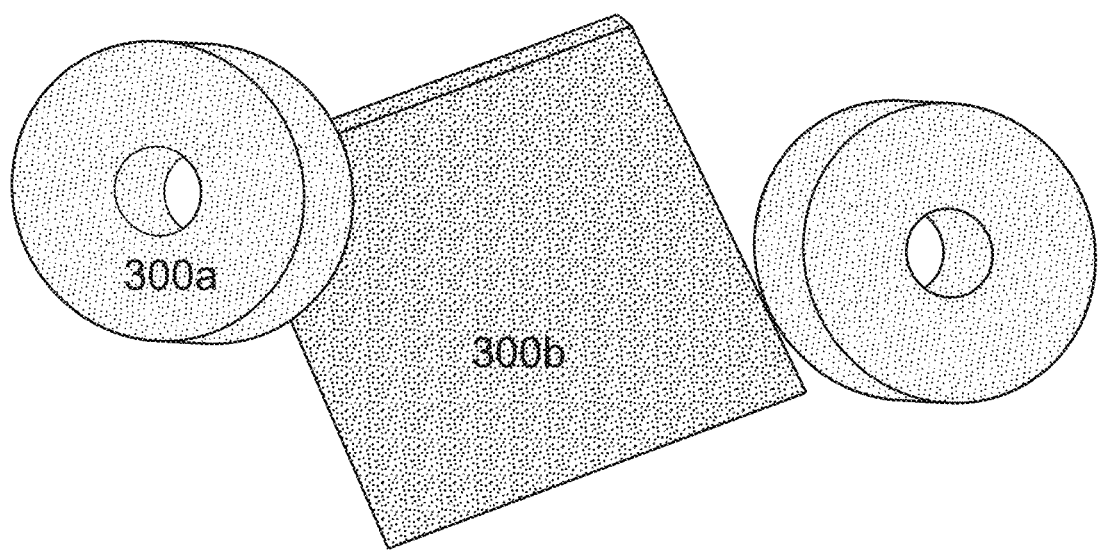
FIG. 2 is a perspective view of various exemplary titanium foams.

In other embodiments, the reinforcement material is in the form of a foam, as depicted in FIGS. 2-5. In some embodiments, the foam is trimmable, as will be described in further detail below. In some embodiments, the porosity and interconnectivity of the foam is important to ensure complete penetration of the dual cement matrix therethrough. In some embodiments, the level and type of porosity of the foam can be tailored based on the type of tooth or application. For example, FIGS. 2-5 depict various foams 300 that may be used. In some embodiments, the foam 300 can take various shapes such as, for example, ring 300a or rectangular 300b, as depicted in FIG. 2. In some embodiments, the foam may have various levels of pores per inch (PPI). FIG. 3 depicts a metal foams 300 c-e having 25 PPI, 35 PPI and 50 PPI, respectively. In some embodiments, the foam has a PPI of from 10 to 60. In other embodiments, the foam has a PPI of from 20 to 60. In other embodiments, the foam has a PPI of from 30 to 60. In other embodiments, the foam has a PPI of from 40 to 60. In other embodiments, the foam has a PPI of from 50 to 60.

In some embodiments, the foam has a PPI of from 10 to 50. In other embodiments, the foam has a PPI of from 10 to 40. In other embodiments, the foam has a PPI of from 10 to 30. In other embodiments, the foam has a PPI of from 10 to 20.

In some embodiments, the foam has a PPI of from 15 to 45. In other embodiments, the foam has a PPI of from 20 to 30. In other embodiments, the foam has a PPI of from 25 to 50. In other embodiments, the foam has a PPI of from 35 to 45. In other embodiments, the foam has a PPI of from 30 to 50.

Figure 4:
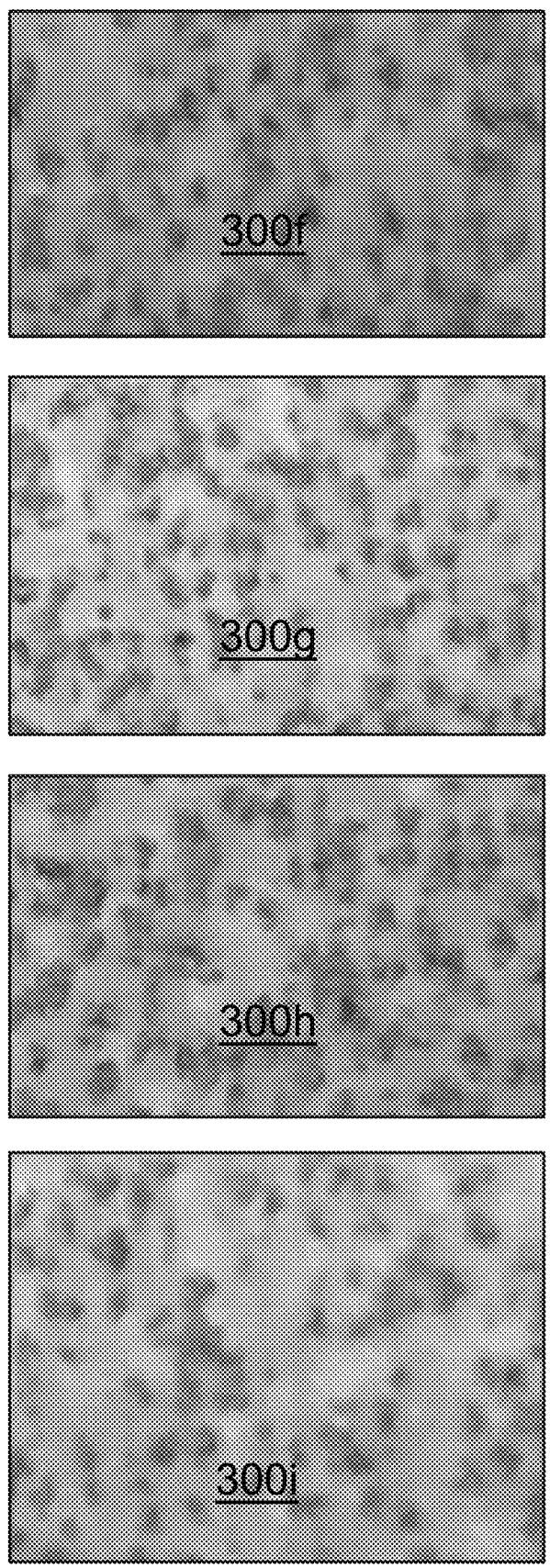
FIG. 4 is a cross-sectional view of a titanium foam mixed with a bioactive cement material according to exemplary embodiments of the present disclosure.

As can be seen in FIG. 4, the porosity and porosity distribution of the foam may be varied as well. For example, the foams 300 f-g have a lower porosity distribution (per centimeter) than foams 300 h-i. To promote penetration of the dual cement matrix through the foam, in some embodiments, the foam has a porosity of 65% to 99%. In other embodiments, the foam has a porosity of 70% to 99%. In other embodiments, the foam has a porosity of 75% to 99%. In other embodiments, the foam has a porosity of 80% to 99%. In other embodiments, the foam has a porosity of 85% to 85%. In other embodiments, the foam has a porosity of 90% to 99%. In other embodiments, the foam has a porosity of 95% to 99%.

Figure 5:
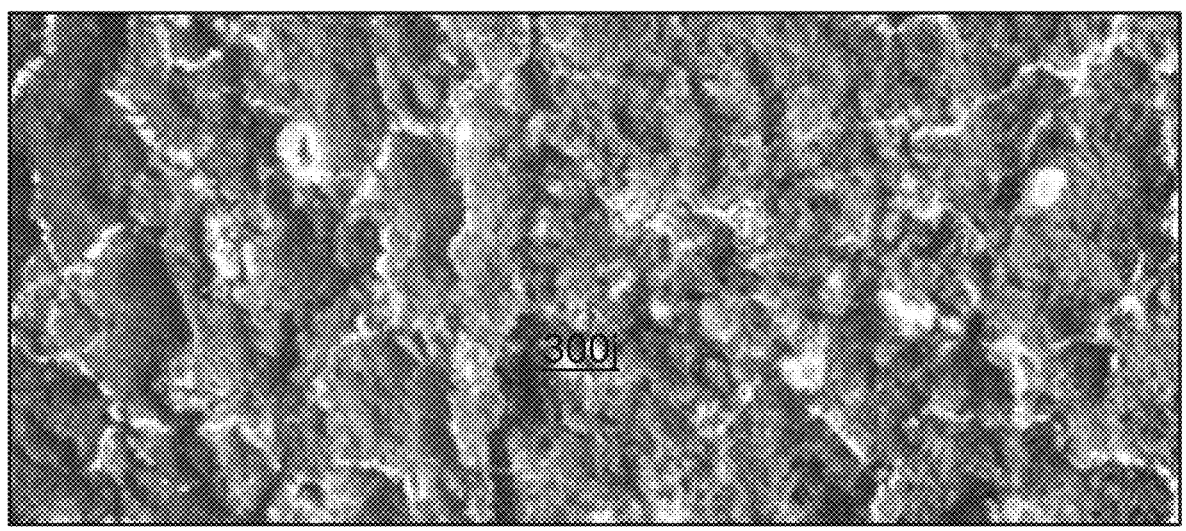
FIG. 5 is a cross-sectional view four exemplary titanium foams according to exemplary embodiments of the present disclosure.

In some embodiments, the foam has a pore size of 25 μm to 750 μm. In other embodiments, the foam has a pore size of 100 μm to 500 μm. In other embodiments, the foam has a pore size of 500 μm to 750 μm. In other embodiments, the foam has a pore size of 100 μm to 250 μm. In other embodiments, the foam has a pore size of 250 μm to 600 μm. In other embodiments, the foam has a pore size of 200 μm to 400 μm. FIG. 5 depicts a reinforcement material 300j with the cement matrix incorporated therein.

In some embodiments, the foam has a porosity of 70% to 95%. In other embodiments, the foam has a porosity of 75% to 85%. In other embodiments, the foam has a porosity of 80% to 90%. In other embodiments, the foam has a porosity of 85% to 95%. In other embodiments, the foam has a porosity of 80% to 85%. In other embodiments, the foam has a porosity of 70% to 90%. In other embodiments, the foam has a porosity of 90% to 95%. In other embodiments, the foam has a porosity of 70% to 85%. In other embodiments, the foam has a porosity of 75% to 95%.

In some embodiments, the foam has a pore size of 5 μm to 1000 μm. In other embodiments, the foam has a pore size of 10 μm to 1000 μm. In other embodiments, the foam has a pore size of 50 μm to 1000 μm. In other embodiments, the foam has a pore size of 100 μm to 1000 μm. In other embodiments, the foam has a pore size of 250 μm to 1000 μm. In other embodiments, the foam has a pore size of 500 μm to 1000 μm. In other embodiments, the foam has a pore size of 750 μm to 1000 μm.

In some embodiments, the foam has a pore size of 5 μm to 750 μm. In other embodiments, the foam has a pore size of 5 μm to 500 μm. In other embodiments, the foam has a pore size of 5 μm to 250 μm. In other embodiments, the foam has a pore size of 5 μm to 100 μm. In other embodiments, the foam has a pore size of 5 μm to 50 μm. In other embodiments, the foam has a pore size of 5 μm to 10 μm.

In some embodiments, the foam has a pore size of 25 μm to 750 μm. In other embodiments, the foam has a pore size of 100 μm to 500 μm. In other embodiments, the foam has a pore size of 500 μm to 750 μm. In other embodiments, the foam has a pore size of 100 μm to 250 μm. In other embodiments, the foam has a pore size of 250 μm to 600 μm. In other embodiments, the foam has a pore size of 200 μm to 400 μm. FIG. 5 depicts a reinforcement material with the cement matrix incorporated therein.

In an exemplary embodiment, the reinforcement material is titanium. Titanium has favorable biocompatibility and physical properties. Furthermore, titanium is more resistant to dissolving in extreme conditions than other types of reinforcement material candidates. During the setting process, the pH of calcium silicate based cements can reach very alkaline (pH-11) levels. Such an alkaline pH will dissolve most types of materials dispersed into the cement material, creating small imperfections in the material. These imperfections inevitably result in weak points in the resulting composite material. Unlike most other materials, titanium and, in particular, the SLA-treated titanium alloys used herein, are able to form a protective $TiO_2$ layer when exposed to air. This $TiO_2$ layer serves as a protective surface coating and improves resistance to corrosion and solubility when the reinforcement material is exposed to the alkaline environment of the dual cement matrix.

In an embodiment, the titanium alloy is $TI_6AL_4V$. $TI_6AL_4V$ is an (α+β) titanium alloy that contains a stabilizer element Al and β stabilizer element V. Typically, the $TI_6AL_4V$ microstructure consists of transformed β containing acicular a as well as a at prior-β grain boundaries, while the annealed wrought $TI_6AL_4V$ bar typically consists of equiaxed a grain plus intergranular β.

In other embodiments, $TI_6AL_4V$ may be replaced with other titanium grades such as $Ti_6Al_7Nb$ and $Ti_5Al_{2.5}Fe$.

The relative amounts of the bioactive cement material to autologous dentin matrix to reinforcement material within the biomimetic composite material can vary depending upon the particular application and other considerations. For example, the autologous dentin matrix can comprise from about 10% by weight to about 20% by weight of the total biomimetic composite material. Additionally, the inorganic reinforcement material can comprise from about 10% by weight to about 35% by weight of the total biomimetic composite material. In an embodiment, the ratio of bioactive cement material to autologous dentin matrix to reinforcement material is 1:1:3.

In some embodiments, the biomimetic composite materials disclosed herein includes at least one additive. Exemplary additives include, but are not limited to: strontium, magnesium, calcium, or phosphate ions. Strontium and magnesium are essential for bone formation and can be used as inorganic trace element additives. In some embodiments, strontium and magnesium are added to the biomimetic composite material via fluid used in the dual cement matrix hydration. In some embodiments, the fluid used for hydration is a water-based liquid or a gel containing either polyethylene glycol, alginate, or another polymer that has the capacity to produce a gel. Furthermore, the inclusion of metal ions such as calcium, magnesium and phosphate ions promote osteogenesis and angiogenesis, thus enhancing bone remodeling and repair processes.

It has been surprisingly found that the disclosed biomimetic composite materials disclosed herein perform very similarly to natural teeth when being prepared with any conventional dental rotary instruments. The biomimetic composite materials are able to be machined and sectioned using diamond or carbide lathes, burs, and discs without unwanted discrimination or separation or the components therein. This good bonding of the bioactive cement materials, the autologous dentin matrix and, in some embodiments, the reinforcement material is due to the flow of the bioactive cement material into dentinal tubules and the reinforcement materials. The dentinal tubules typically have a diameter from 1 to 3 microns in sized. On each dentin particle, there is a minimum of several hundred exposed tubules which creates a durable interlocking composite network without the need for any adhesives.

When compared to other implant materials, the disclosed biomimetic composite materials are much closer in composition, color and mechanical properties, to a natural tooth. The biomimetic composite material mimics the mechanical properties of natural teeth in terms of mechanical strength and biocompatibility, and can be used as a dentin substitute due to its favorable long-term mechanical and antibacterial properties. The mechanical properties of the biomimetic composite materials disclosed herein are intended to be closer to the range of human dentin and bone than conventional implant materials. Specifically, the mismatch of material mechanical properties between conventional metal/zirconia screw type implants and the surrounding bone has been extensively documented in dental and orthopedic literature. The change in stress distribution from dynamic forces at the bone to implant interface, also known as stress shielding, is a significant issue that may contribute to high rates of implant failures. By matching the disclosed biomimetic composite material properties more closely to native tissues, the current disclosure provides a more natural distribution of multi-axial stresses results.

Manufacturing Methods

Figure 6:
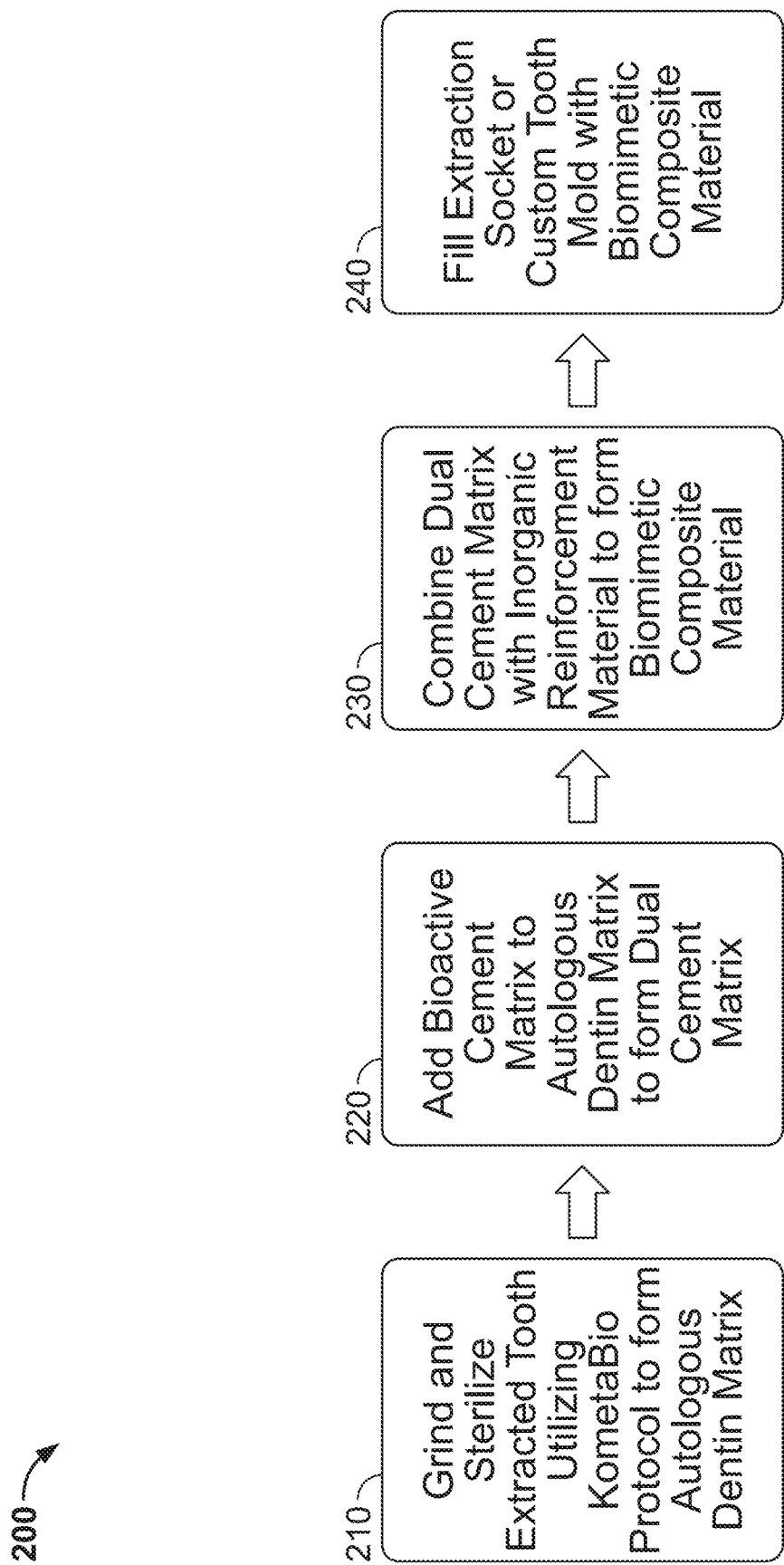
FIG. 6 is a flowchart setting forth the steps of an exemplary method of forming a biomimetic composite material according to exemplary embodiments of the present disclosure.

The above-described biomimetic material can be manufactured using any number of different suitable techniques. FIG. 6 illustrates a process for manufacturing the biomimetic composite material 200 in accordance with an exemplary embodiment of the present disclosure.

In step one 210, the autologous dentin matrix is formed by subjecting an extracted tooth to a process that grinds and sterilizes the extracted tooth. In some embodiments, dentin particles are produced from a tooth using a commercially available dentin grinder machine such as the Smart Dentin Grinder from Kometabio.

During the process, decay and filling material as well as the enamel and cementum is initially removed with a highspeed rotary bur. The tooth is then dried and placed into the dentin grinder machine, which grinds the tooth into small particles. The particles are collected in two chambers below the grinding cartridge and sterilized using a chemical sterilization process of NaOH and ethanol solution wash followed by multiple washes with a phosphate buffered solution and distilled water. The particles are then dried with sterile gauze and a hot plate, if needed.

The above-described protocol and equipment allows autologous dentin to be produced. By grinding the extracted tooth, dentin in particle form is produced and is subsequently used in making the biomimetic composite material. In some embodiments, the dentin particles are treated with Vitamin C for 5-10 minutes prior to mixing with the bioactive cement material to prevent the dentin particles from dissolving during the high pH setting reaction of the bioactive cement material.

In step two 220, once the dentin is processed, the bioactive cement material is added to the autologous dentin matrix according to desired ratios to form the dual cement matrix. In some embodiments, other ingredients, such as water and additives, are added to the dual cement matrix. The materials are then mixed using conventional equipment, such as a dental triturator.

In one example, the mixing process includes the following steps:
1. 700.2 mg of dentin powder is added to 700 mg of cement powder in a capsule.
2. The capsule is placed in a dental triturator and mulled for 10 seconds to mix the two powder components.
3. The capsule is removed from the triturator and 7 drops of liquid from a pipette are added in the capsule.
4. The capsule is placed back in the triturator and triturated at a minimum speed of 4,000 rpm for 30 seconds.

In some embodiments, the dual cement matrix is chemically sterilized with injectable Ascorbic Acid [1:1].

In step three 230, once the dual cement matrix has been formed, it is combined with the reinforcement material prior to setting.

Figure 7:
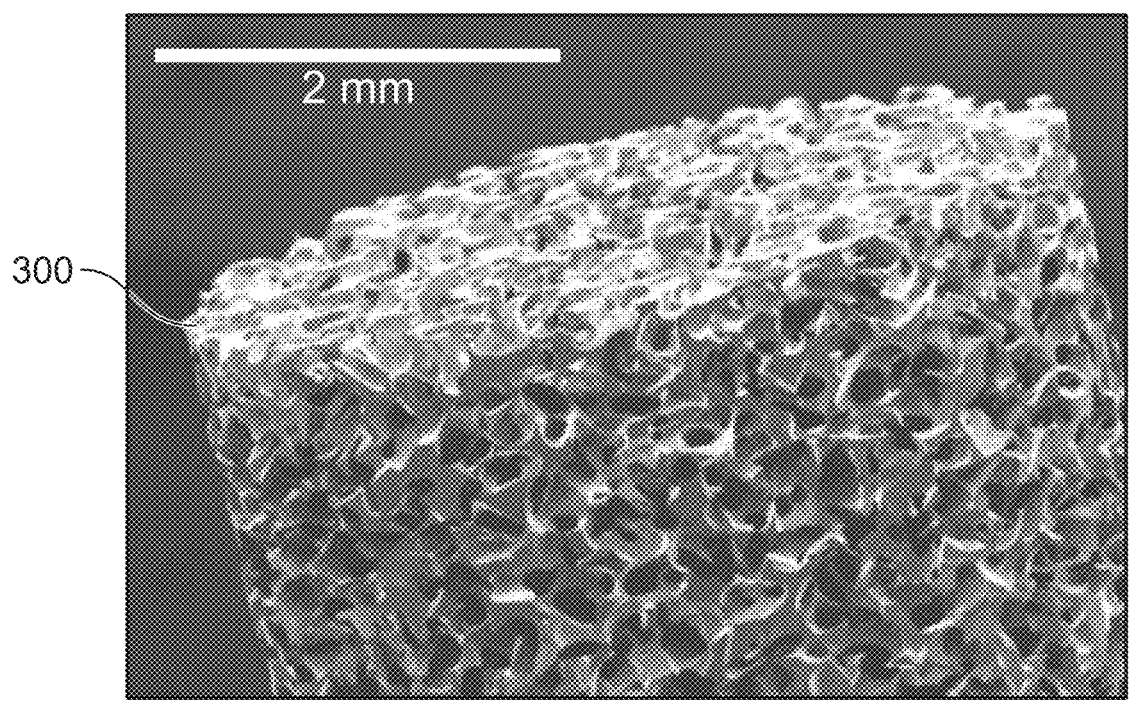
FIG. 7 is a view of a titanium foam reinforcement material according to an exemplary embodiment of the present disclosure.

In some embodiments, as described above, the reinforcement material is in the form of a prefabricated foam. In an exemplary embodiment, the foam is a titanium foam produced by a powder metallurgical process using a space holder method. An exemplary sample titanium foam 300 is depicted in FIG. 7. In one example, the titanium foam is produced according to the following steps:
1. Mixing of fine titanium powder with a space holder substance;
2. Pressing of a green body;
3. Removal of the space holder substance; and
4. Sintering.

In some embodiments, the titanium powder is a commercially pure (cp) titanium grade 4 according to the ASTM standard F1580-01. In some embodiments, the grain size of the titanium powder follows a log-normal distribution with an average d50-value of 25-40 µm. In some embodiments, the space holder substance is ammoniumhydrogencarbonate $(NH_4)HCO_3$, according to the British pharmacopoeia BP E503. In some embodiments, the desired grain size of the space holder particles (425-710 µm) is obtained by sieving. This grain size is chosen to achieve a final pore size in the approximate range of 100-500 µm, which is known to result in a consistent tissue response and rapid bone formation. In some embodiments, the total porosity of the titanium foam is adjusted to the range of 65-99% by adding an adequate amount of the space holder particles. The two powders are mixed in a proprietary process using tumbling glass bottles. The green bodies are pressed with two different compaction methods: cold-isostatic and uniaxial.

In some embodiments, the titanium foam is treated to increase wettability thereof. Because titanium foam is a hydrophobe, it is difficult to mix with the dual cement matrix and may not be distributed through some portions of the dual cement matrix. To increase wettability, in some embodiments, the titanium foam is grit-blasted and acid-etched to make the surface SLA, and further processed to a high degree of hydrophilicity. The protocol for the SLA treatment is previously described by Wennerberg. Acid attack of the surface of dental implants, as in SLA treatment, results in uniform roughness with pits and craters of micrometric size, leading to an increase in surface area. In these pits, osteoblasts and supportive connective tissue can migrate, resulting an enhancement in bioadhesion. In other embodiments, the wettability of the titanium foam is increased by other methods or treatments.

Each manufacturer has its own method of acid etching by controlling the temperature, concentration of acids, and exposure time. SLA implants are often used in clinical practice. One aim of the present disclosure is to determine a proper preparation technique for the surface of SLA dental implants, in the absence of detailed specification of manufacturing process of commercially available implants. By controlling the disclosed acid etching process with regard to mixture of acids used, concentration, temperature, exposure time, $Ti_6Al_4V$ dental implants with a moderately rough topography and good hydrophilic properties are obtained.

Figure 8:
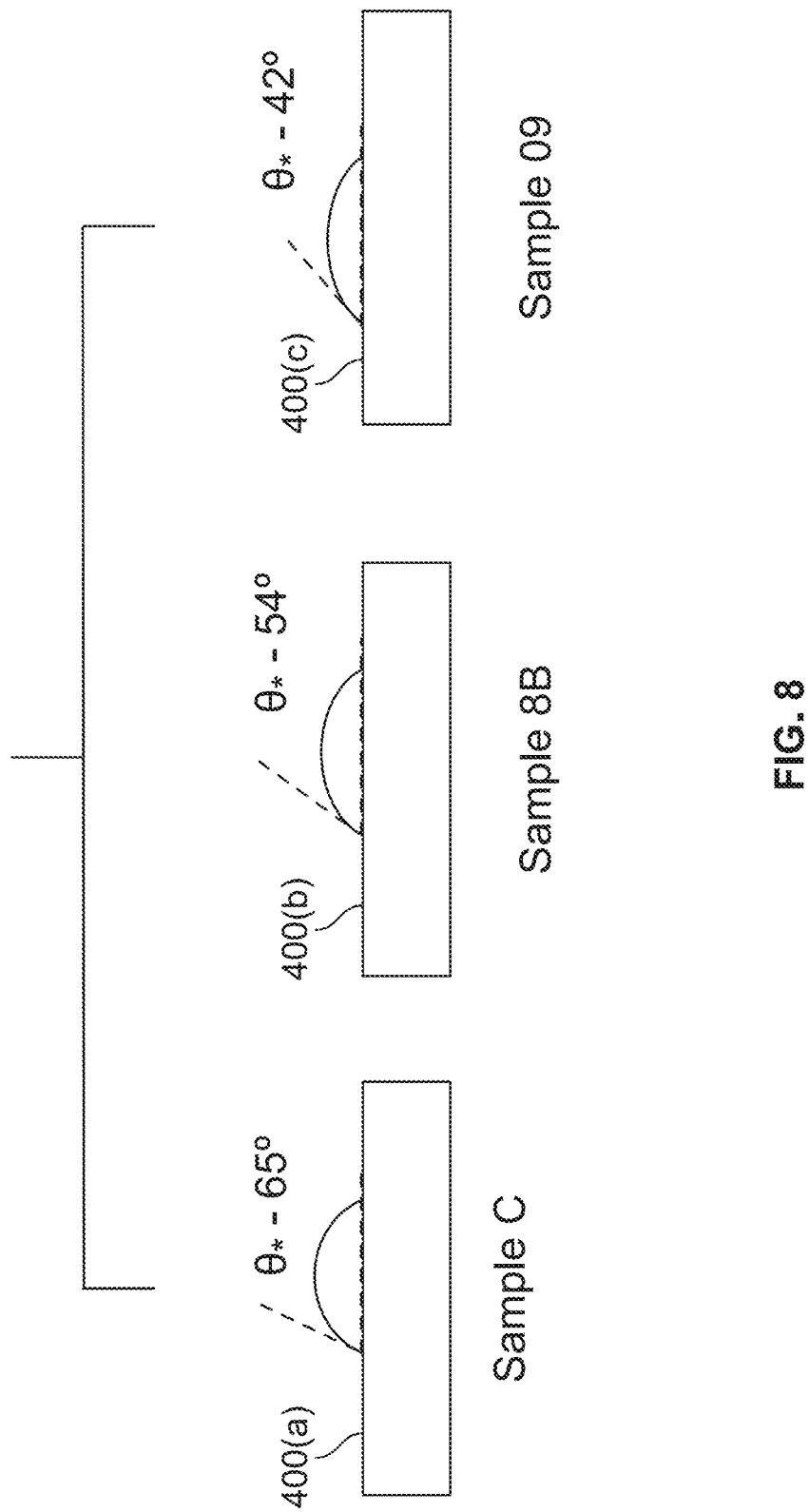
FIG. 8 is a perspective view of the wettability of a machined, sand blasted, and sand blasted and acid etched $Ti_6Al_4V$ surfaces.

Specifically, an exemplary protocol for increasing the wettability of titanium reinforcement materials, according to an embodiment of the present disclosure, includes subjecting the reinforcement material to acid etch using HClIn, $H_2SO_4$In, or a combination of HCl and $H_2SO_4$ (1:1). In some embodiments, the concentration of acid solution is 4.9% sulfuric acid and 3.65% hydrochloric acid. FIG. 8 depicts the wettability of a machined Ti$_6$Al$_4$V surface 400(*a*), a sand blasted Ti$_6$Al$_4$V surface 400(*b*), and a sand blasted and acid etched Ti$_6$Al$_4$V surface 400(*c*) in increasing order from left to right.

Once the reinforcement foam is formed, it may be stored in synthetic tissue fluid. Before clinical application, the clinician can cut, shape and trim the foam to a desired shape. The reinforcement foam is then combined with the dual cement matrix and the resulting implant is placed in the tooth socket. In some embodiments, additional dual cement matrix is packed into the socket to ensure that the implant is intimately adapted to the tooth socket.

In other embodiments, as described above, the dual cement matrix is combined with a reinforcement material in the form of reinforcement particles. In these embodiments, the reinforcement material is prepared for in situ mixing with the cement matrix.

In some embodiments, the reinforcement material is in the form of titanium micro rods having a length of 200 to 500 µm and a diameter of 10 to 100 µm. The titanium micro rods can be prepared by various different methods such as, for example, electrospinning or mechanical grinding. Similar to the titanium foam reinforcement material, in some embodiments, the titanium micro rods are SLA treated to increase wettability thereof. Specifically, the same grit-blasting and acid-etching protocol described above may be used to increase the wettability of the micro rods.

Once the reinforcement particles are formed, they can be added to the dual cement matrix during mixing. In step four 240, the resulting paste may then be used to fill the extraction socket or in a custom patient specific tooth mold (described below).

Customized Tooth Form Implants

Figure 9:
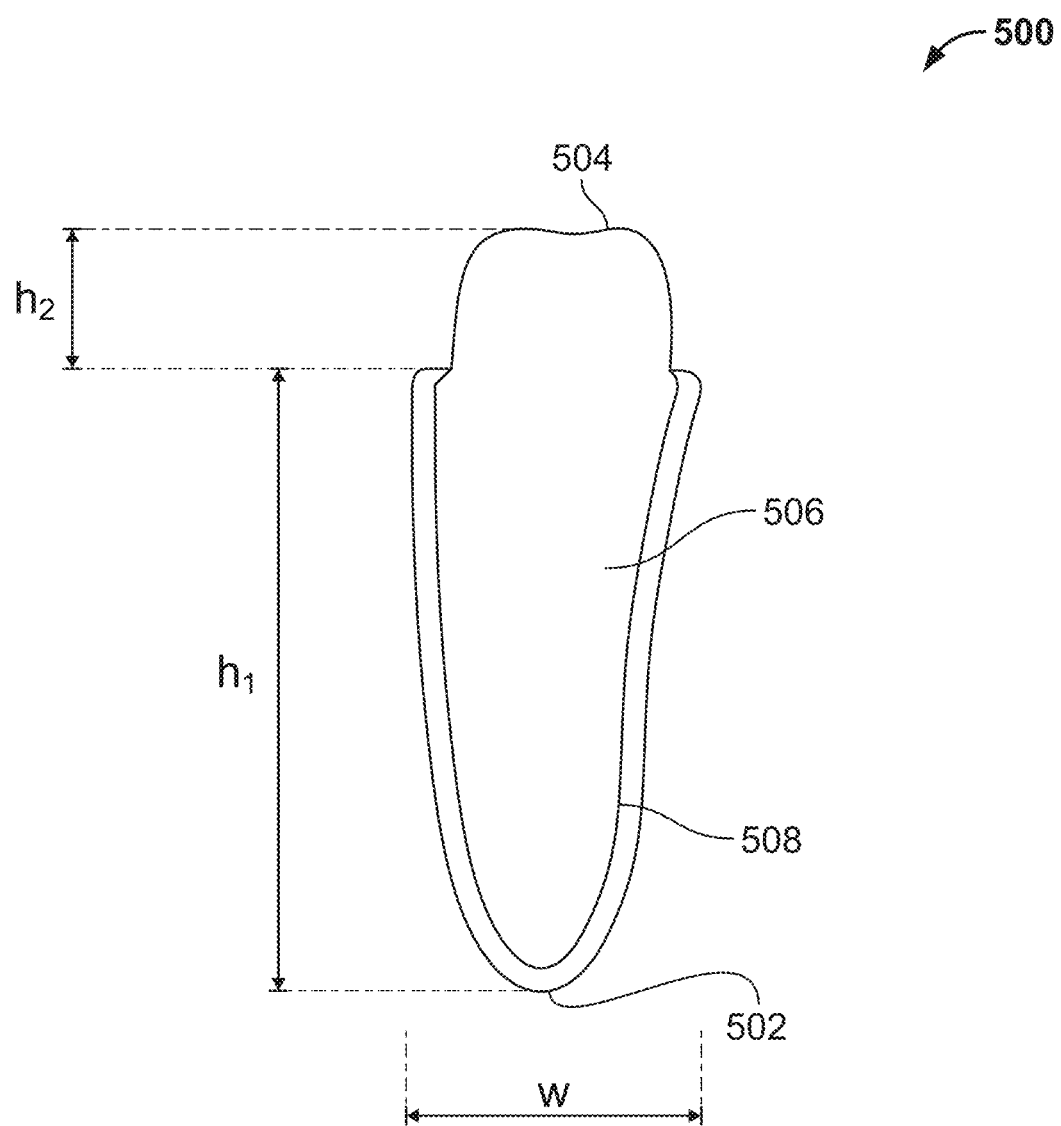
FIG. 9 is a cross-sectional view of a first tooth form implant in the form of an incisor/canine implant according to exemplary embodiments of the present disclosure.
Figure 10:
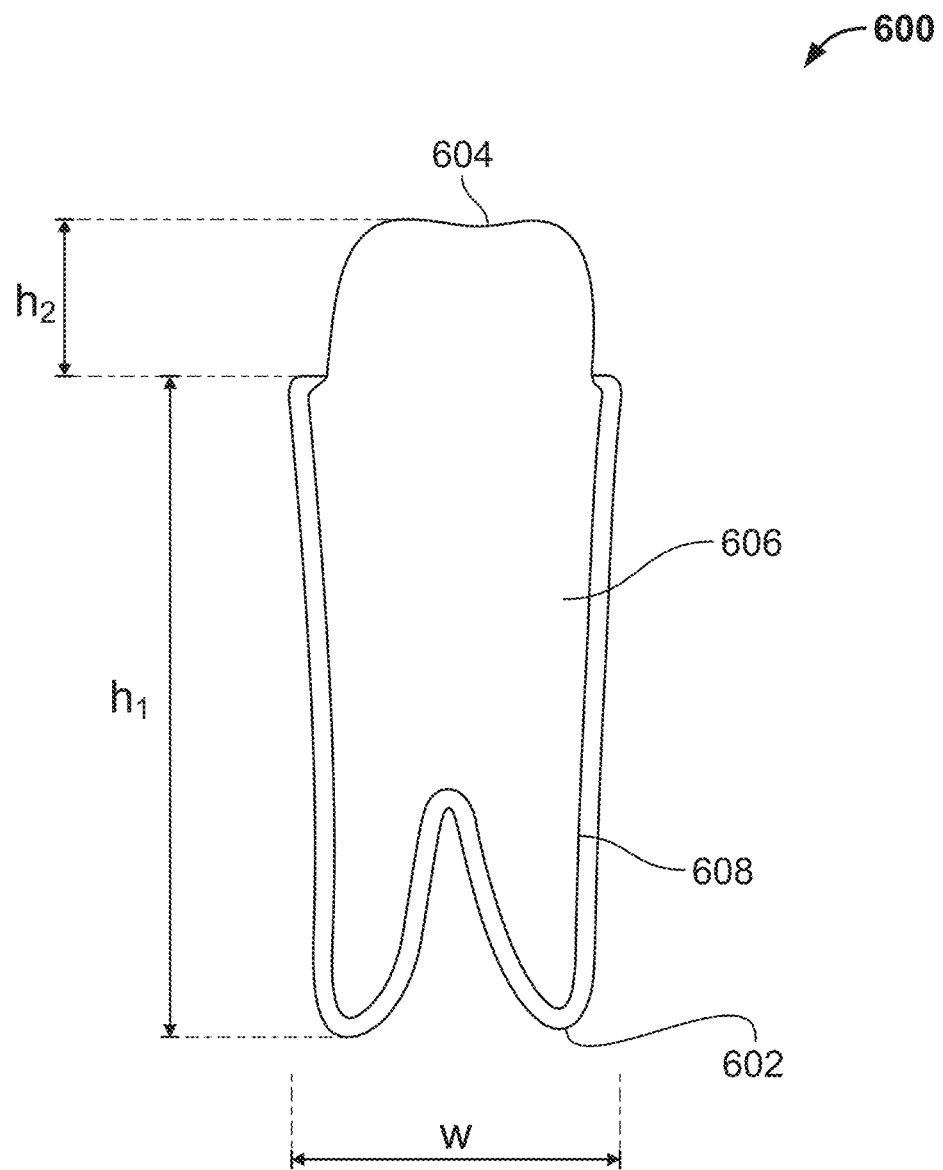
FIG. 10 is a cross-sectional view of a second tooth form implant in the form of a premolar according to exemplary embodiments of the present disclosure.
Figure 11:
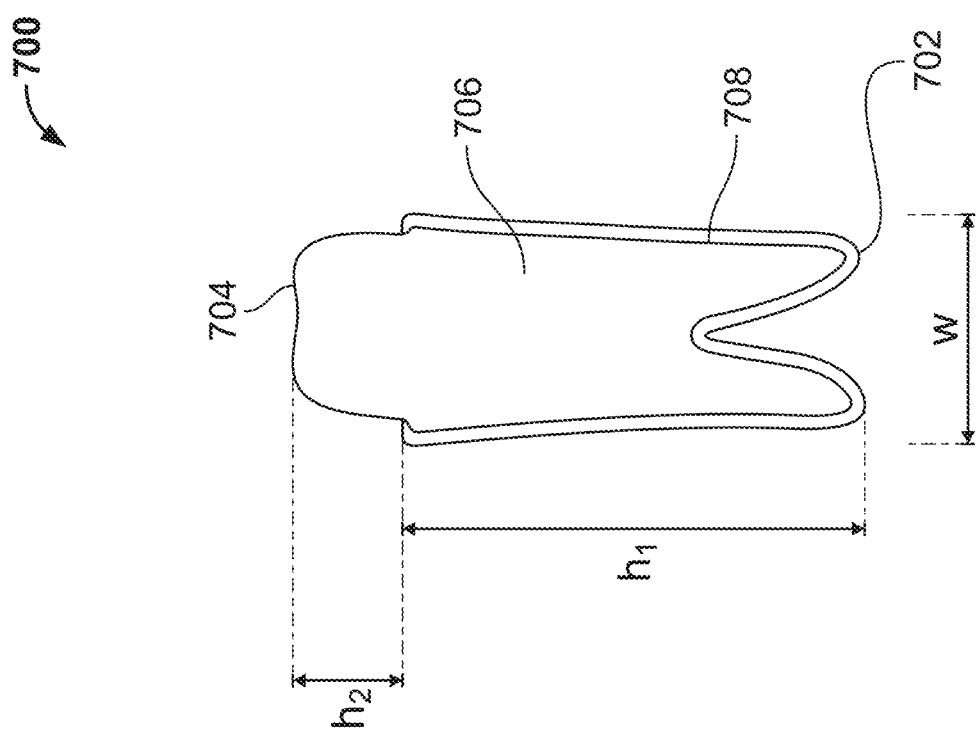
FIG. 11 is a cross-sectional view of a third tooth form implant in the form of a molar according to exemplary embodiments of the present disclosure.

FIGS. 9-11 depict a number of different customized tooth form implants having different shapes and sizes. More particularly, FIG. 9. depicts a first tooth form implant 500 in the form of an incisor/canine tooth implant, according to an embodiment of the present disclosure. The implant 500 has a root portion 502 and a crown portion 504. As described herein, the implant 500 is constructed in view of the anatomy of a patient and in particular, the size and shape of the implant 500 is intended to mimic an extracted or otherwise missing tooth. In some embodiments, the height (length) h$_1$ of the first portion root portion 502 is between about 12 mm to about 18 mm and the height (length) h$_2$ of the crown portion 504 is between about 3 mm and about 8 mm. The width (apex to cervix) w can be between about 1 mm to about 9 mm.

In some embodiments, the implant 500 includes a core 506 and an outer layer 508 surrounding the core 506. In some embodiments, the outer layer 508 covers an entire surface area of the core 506. In other embodiments, the outer layer 508 covers a portion of the surface area of the core 506. In some embodiments the core 506 is formed of a first material while the outer layer 508 is formed of a second material that is different than the first material.

In some embodiments, a thickness of the core 506 is greater than a thickness of the outer layer 508. As defined herein, a "thickness" is a dimension between two lateral surfaces of the component. In some embodiments, the thickness of the core 506 is from 1 mm to 10 mm. In some embodiments, a thickness of the outer layer 508 is from 500 µm to 1500 µm.

In some embodiments, the core 506 comprises the bioactive cement material disclosed herein. In some embodiments, the core 506 comprises 100% of the bioactive cement material. In some embodiments, the outer layer 508 comprises a biomimetic composite material disclosed herein. In some embodiments, the core 506 and the outer layer 508 comprise a biomimetic composite material. In some embodiments, the core 506 and the outer layer 508 comprise a biomimetic composite material with different ratios of the bioactive cement material, autologous dentin matrix and inorganic nano-reinforcement fiber. In other embodiments, the core 506 and the outer layer 508 comprise a biomimetic composite material with the same ratio of the bioactive cement material, autologous dentin matrix and inorganic nano-reinforcement fiber.

FIG. 10 depicts a second tooth form implant 600 in the form of a premolar tooth implant, according to an embodiment of the present disclosure. The second tooth implant 600 has a root portion 602 and a crown portion 604. As described herein, the implant 600 is constructed in view of the anatomy of a patient and in particular, the size and shape of the implant 600 is intended to mimic an extracted or otherwise missing tooth. In one exemplary embodiment, the height (length) h$_1$ of the root portion 602 is between about 12 mm to about 18 mm and the height (length) h$_2$ of the crown portion 604 is between about 3 mm and about 8 mm. The width (apex to cervix) w can be between about 1 mm to about 9 mm.

In some embodiments, the implant 600 includes a core 606 and an outer layer 608 surrounding the core 606. In some embodiments, the outer layer 608 covers an entire surface area of the core 606. In other embodiments, the outer layer 608 covers a portion of the surface area of the core 606. In some embodiments the core 606 is formed of a first material while the outer layer 608 is formed of a second material that is different than the first material.

In some embodiments, a thickness of the core 606 is greater than a thickness of the outer layer 608. In some embodiments, the thickness of the core 606 is from 1 mm to 10 mm. In some embodiments, a thickness of the outer layer 608 is from 500 µm to 1500 µm.

In some embodiments, the core 606 comprises the bioactive cement material disclosed herein. In some embodiments, the core 606 comprises 100% of the bioactive cement material. In some embodiments, the outer layer 608 comprises a biomimetic composite material disclosed herein. In some embodiments, the core 606 and the outer layer 608 comprise a biomimetic composite material. In some embodiments, the core 606 and the outer layer 608 comprise a biomimetic composite material with different ratios of the bioactive cement material, autologous dentin matrix and inorganic nano-reinforcement fiber. In other embodiments, the core 606 and the outer layer 608 comprise a biomimetic composite material with the same ratio of the bioactive cement material, autologous dentin matrix and inorganic nano-reinforcement fiber.

When FIG. 10 depicts the second tooth form implant 600 having a pair of root structures, it will be understood that the second tooth form implant 600 may have only a single root structure. The implants may be designed with more than one root. As long as the path of insertion is not hindered by their divergence and assuming that having multiple roots would be beneficial in stabilizing the implant. In some cases, it may be beneficial to fabricate an implant with fewer roots or reduce the curvature of the roots to facilitate the implantation process.

FIG. 11 depicts a third tooth form implant 700 in the form of a molar tooth implant, according to an embodiment of the present disclosure. The third tooth implant 700 has a root portion 702 and a crown portion 704. As described herein, the implant 700 is constructed in view of the anatomy of a patient and in particular, the size and shape of the implant 700 is intended to mimic an extracted or otherwise missing tooth. In one exemplary embodiment, the height (length) $h_1$ of the root portion 702 is between about 12 mm to about 18 mm and the height (length) $h_2$ of the crown portion 704 is between about 3 mm and about 8 mm. The width (apex to cervix) w can be between about 1 mm to about 13 mm.

In some embodiments, the implant 700 includes a core 706 and an outer layer 708 surrounding the core 706. In some embodiments, the outer layer 708 covers an entire surface area of the core 706. In other embodiments, the outer layer 708 covers a portion of the surface area of the core 706. In some embodiments the core 706 is formed of a first material while the outer layer 708 is formed of a second material that is different than the first material.

In some embodiments, a thickness of the core 706 is greater than a thickness of the outer layer 708. In some embodiments, the thickness of the core 706 is from 1 mm to 10 mm. In some embodiments, a thickness of the outer layer 708 is from 500 μm to 1500 μm.

In some embodiments, the core 706 comprises the bioactive cement material disclosed herein. In some embodiments, the core 706 comprises 100% of the bioactive cement material. In some embodiments, the outer layer 708 comprises a biomimetic composite material disclosed herein. In some embodiments, the core 706 and the outer layer 708 comprise a biomimetic composite material. In some embodiments, the core 706 and the outer layer 708 comprise a biomimetic composite material with different ratios of the bioactive cement material, autologous dentin matrix and inorganic nano-reinforcement fiber. In other embodiments, the core 706 and the outer layer 608 comprise a biomimetic composite material with the same ratio of the bioactive cement material, autologous dentin matrix and inorganic nano-reinforcement fiber.

When FIG. 11 depicts the third tooth form implant 700 having a pair of root structures, it will be understood that the third tooth form implant 700 may have only a single root structure. The implants may be designed with more than one root. As long as the path of insertion is not hindered by their divergence and assuming that having multiple roots would be beneficial in stabilizing the implant. In some cases, it may be beneficial to fabricate an implant with fewer roots or reduce the curvature of the roots to facilitate the implantation process.

Manufacture of Tooth Form Implants

Figure 12:
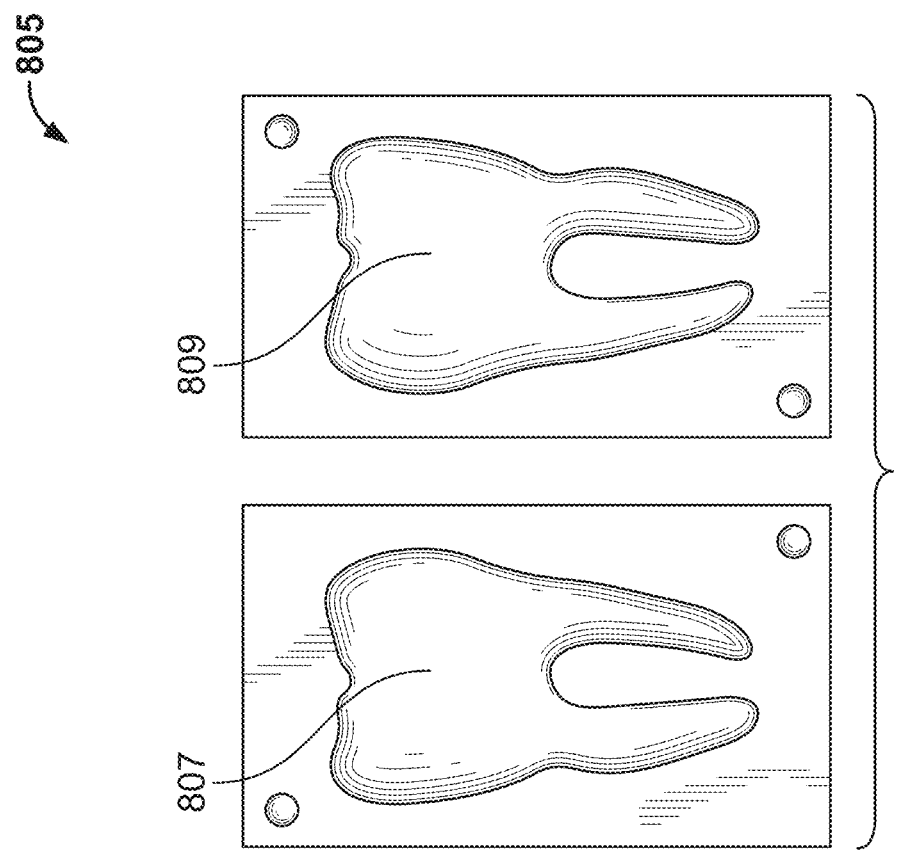
FIG. 12 is a view of molds created by an additive manufacturing technique (e.g., 3D printing) according to exemplary embodiments of the present disclosure.
Figure 13:
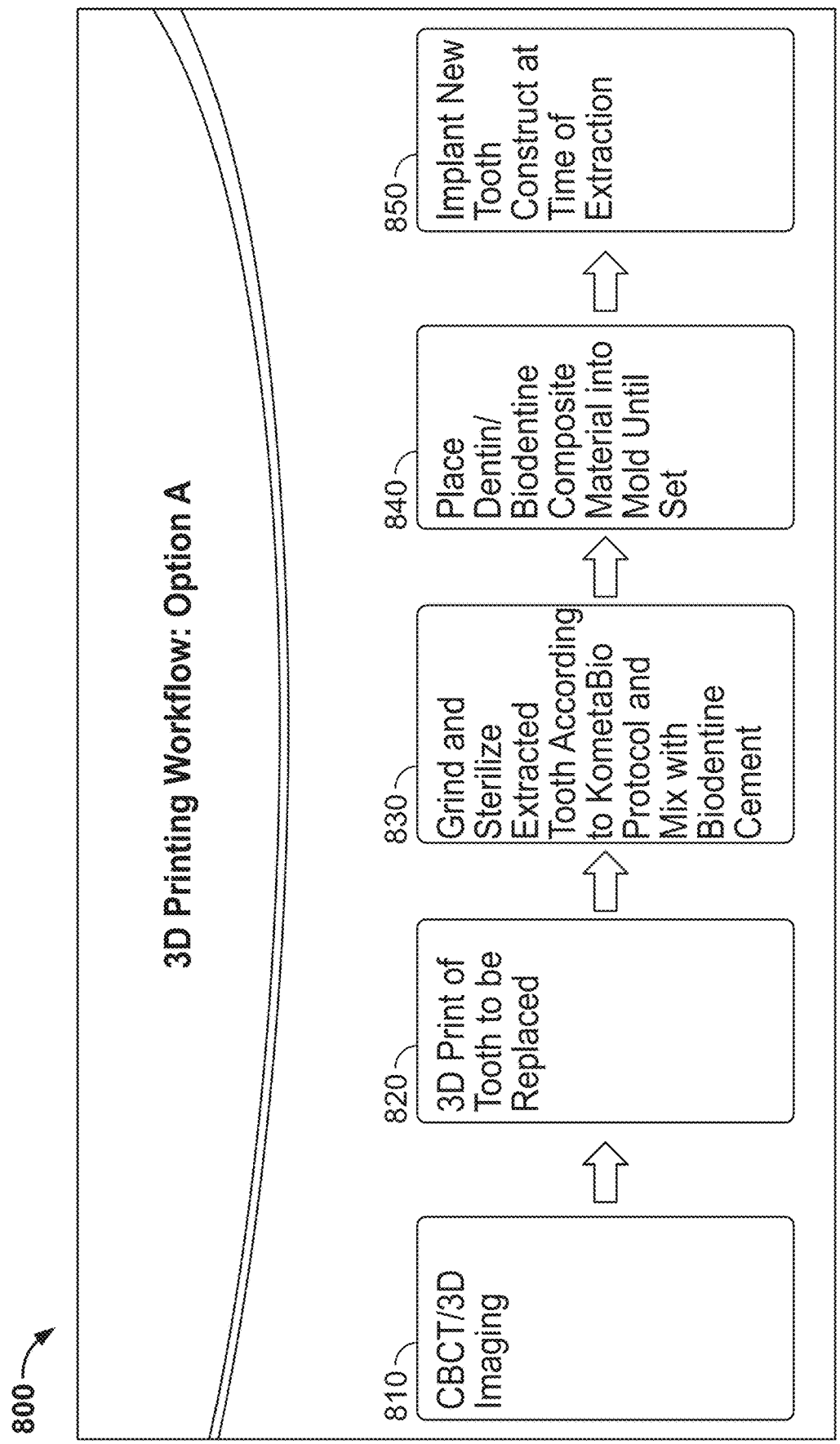
FIG. 13 is a flowchart setting forth the steps of a 3D printing process used to form a customized tooth form implant according to exemplary embodiments of the present disclosure.

FIGS. 12-13 illustrate an exemplary process for manufacturing a customized tooth form implant in accordance with exemplary embodiments of the present disclosure.

FIG. 13 is a flowchart depicting exemplary steps involved with a first method 800 for manufacturing a customized tooth form implant.

The first method 800 includes a first step 810 of performing a CBCT/3D imaging of a tooth that is to be replaced by the customized tooth form implant. The imaging results are stored in a computer file or the like.

As is known in the art, dental cone beam computed tomography (CT) is a special type of x-ray equipment used when regular dental or facial x-rays are not sufficient. This technology allows three dimensional (3-D) images of teeth, soft tissues, nerve pathways and bone to be produced in a single scan. It will be understood that other types of imaging can be used in order to generate a customized computer-generated model of a person's tooth.

In a second step 820, an additive manufacturing process (3D print mold) is used to produce a customized mold 805 that is shown in FIG. 12, as is based upon the imaging performed in step 810. The customized mold 805 is formed of a first mold cavity 807 (i.e., a first mold half) and a second mold cavity 809 (i.e., a second mold half). As is known in the art, when the first and second mold cavities 807, 809 are combined, a complete mold 805 is formed with the hollow cavities of the mold defining the space that receives the material that forms the tooth form implant and thus is formed using additive manufacturing (3D printing) so as to match the shape and size of the tooth to be replaced with the customized tooth form implant.

One or both of the first mold cavity 807 and second mold cavity 609 includes an inlet port for injecting material into the mold 805 when it is in the closed position.

In a third step 830, a biomimetic composite material that is described above is prepared by the methods described above.

Figure 14:
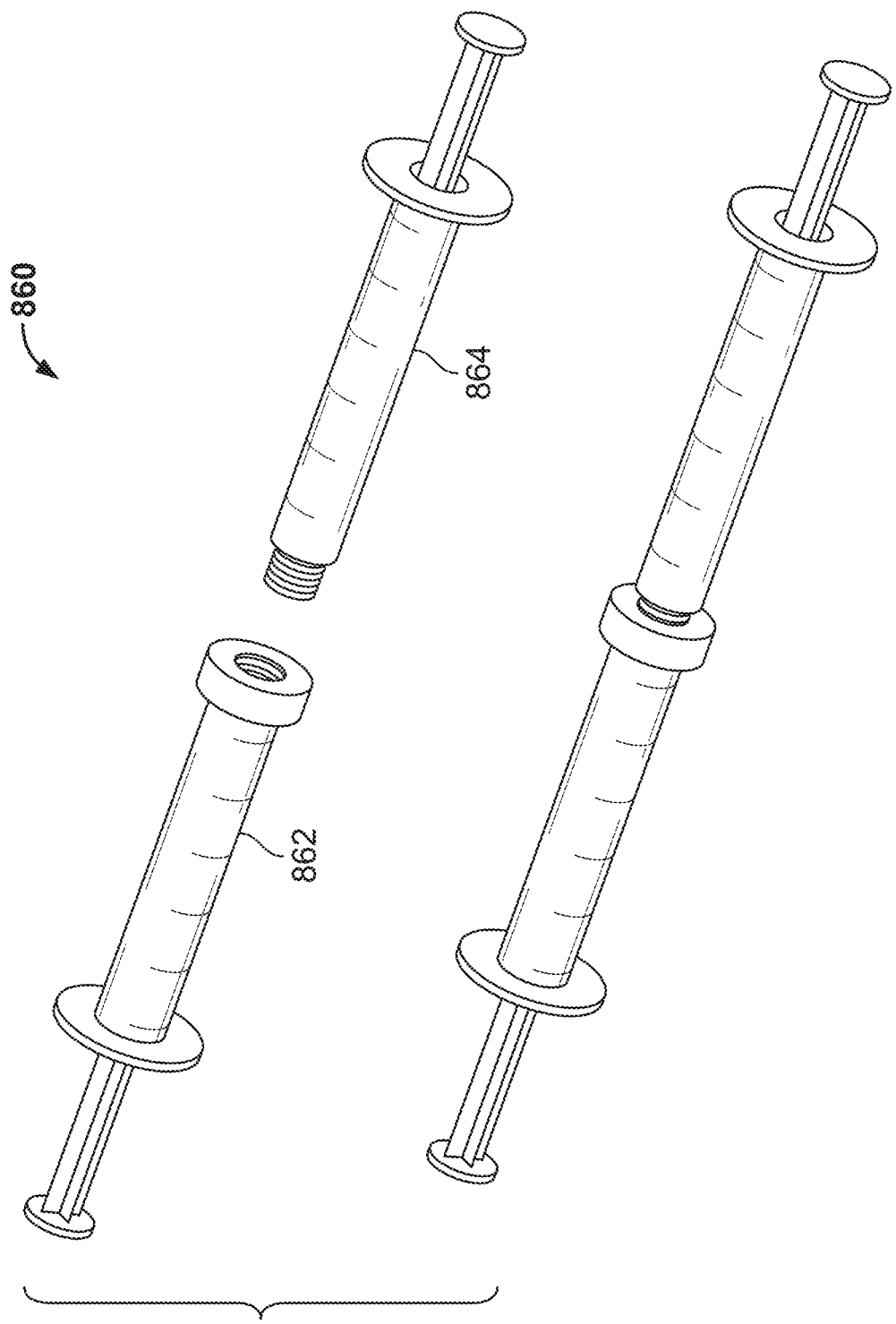
FIG. 14 is a perspective view of a pair of interlocking syringes that can be used for mixing the composite materials according to exemplary embodiments of the present disclosure.

FIG. 14 illustrates an alternative technique to using a dental triturator. More specifically, FIG. 14 depicts a device 860 that is formed of a first syringe 862 and a second syringe 864 that are configured to interlock with one another. The first syringe 862 contains the bioactive cement (e.g., in paste form) and the second syringe 864 contains the processed dentin particles. The bioactive cement material and the dentin particles are thus added to the back end of the separate syringes 862, 864 to a specific measurement. The two syringes 862, 864 are attached to each other and the two materials can be mixed manually until a uniform composite mixture is formed.

In a fourth step 840, the biomimetic composite materials used to form the tooth form implant are added to the mold 805. When the tooth form implant includes both a core formed of the bioactive cement only and an outer layer formed of the biomimetic composite material, the biomimetic composite material is added to the open first and second mold cavities 807, 809 so as to effectively coat the exposed surfaces that are within the respect cavities and which define the outer surfaces of the tooth form implant. The biomimetic composite material is then allowed to set so as to form a hardened coating within the mold cavities. The biomimetic composite material may not need to be fully set before closing the mold and adding the core material. Both options may be possible. Next, the two mold cavities 807, 809 are closed so as to define a hollow space inside of the set composite material. The bioactive cement material is then added through the inlet port into this hollow space inside of the set composite material, thereby forming the core of the tooth form implant. The core and outer layer are bonded to one another to form a solid implant.

In a fifth step 850, the new tooth construct (tooth form implant) is then implanted into the patient's mouth. One of the advantages of the present invention is that in the event that the processed dentin comes from the patient, all of the foregoing steps 810-840 can be done at the time of the tooth extraction. Moreover, the new tooth construct is customized for the specific patient.

It will be appreciated that while the above-described additive manufacture process can be described as creating a negative of the tooth construct (i.e., the mold), an additive manufacturing process can be used to generate and form the positive of the tooth and then the mold can be made using a suitable molding material, such as putty or elastomeric materials to form a mold identical or similar to the one illustrated herein.

In other words, and with some similarity to the steps disclosed in FIG. 13, this alternative method can include a first step of performing a CBCT/3D imaging of a tooth that is to be replaced by the customized tooth form implant. The imaging results are stored in a computer file or the like. It will be understood that other types of imaging can be used in order to generate a customized computer-generated model of a person's tooth.

In a second step, an additive manufacturing process (3D print mold) is used to produce a customized tooth (positive 3D print of the tooth) and then a custom mold can be fabricated using a mold material, such as putty or an elastomeric material, that is placed over the 3D printed tooth. This mold is then used in the manner described herein to form the custom tooth implant.

Moreover, an extrusion-based technique (e.g., FDM-fused deposition modeling or bioplotters) can be used to form ("print") the biomimetic composite materials (tooth form implants) directly without the use of a mold. This technique involves two low temperature print heads to print both the cement core and the composite surface layer. In other words, one print head can be used for formation of the cement core and the second print head can be used for formation of the composite surface layer.

Custom Milling Technique

FIGS. 15A-15C and 16 illustrate another exemplary process for manufacturing a customized tooth form implant in accordance with the present invention and more particularly, a custom milling process can be used as part of the manufacturing method.

Figure 16:
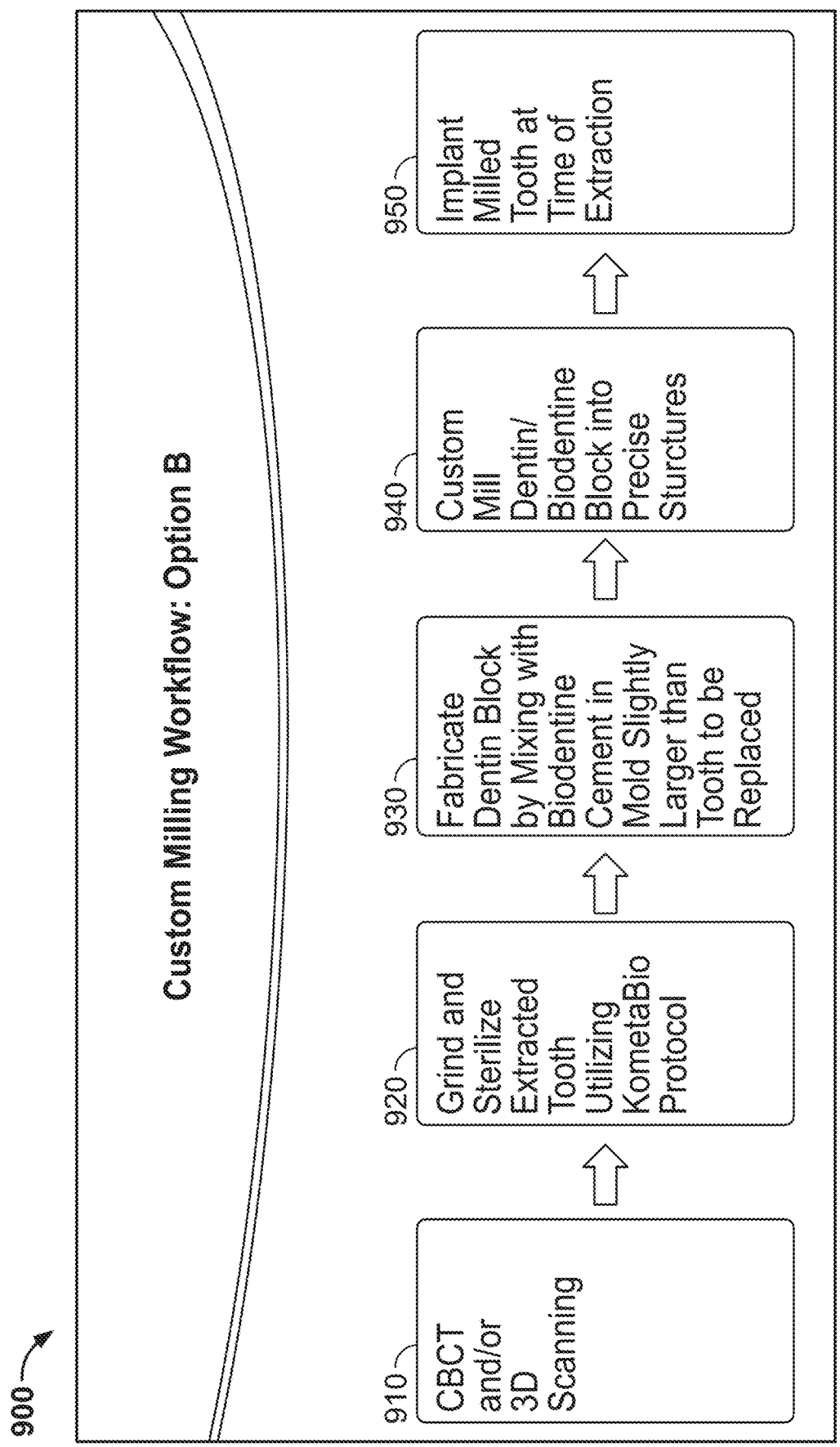
FIG. 16 is a flowchart setting forth the steps of a custom milling process used to form a customized tooth form implant according to exemplary embodiments of the present disclosure.

FIG. 16 is a flowchart showing exemplary steps involved with a second method 900 for manufacturing a customized tooth form implant.

The second method 900 includes a first step 910 of performing a CBCT/3D imaging of a tooth that is to be replaced by the customized tooth form implant. The imaging results are stored in a computer file or the like. As with the previous method, other imaging techniques can be used.

In a second step 920, the extracted tooth is subjected to a process that grinds and sterilizes the extracted tooth and more particularly, a Smart Dentin Grinder and the Komet-aBio protocol can be used to form the processed dentin in particulate form.

In a third step 930 and with reference to FIG. 15A, a dentine block 932 is formed by casting the biomimetic composite material of the present invention into a rectangular mold with a mount 934 present that will allow for attaching into a milling machine. The mount 934 can be a metal mount/jig that is configured for insertion into a milling unit to secure the cast (dentine) block 932. The mold (rectangular mold) that is used to cast the dentine block 932 is constructed to be slightly larger than the tooth to be replaced.

In a fourth step 940, the hardened composite dentine block 932 is loaded into a milling unit and, based on data from the imaging of step 910 (e.g., CAD data), the 3D custom tooth form implant is milled from the composite dentine block 932 as shown in FIG. 15B.

In a fifth step 950, the custom tooth form implant formed by milling is then implanted and as mentioned with respect to the previous embodiment, the implantation, at least in one embodiment, can be performed at the time of extraction. As shown in FIG. 15C, the supporting mount 934 can be removed prior to or during insertion of the custom tooth form implant.

Elastomeric Casting Technique

Figure 17:
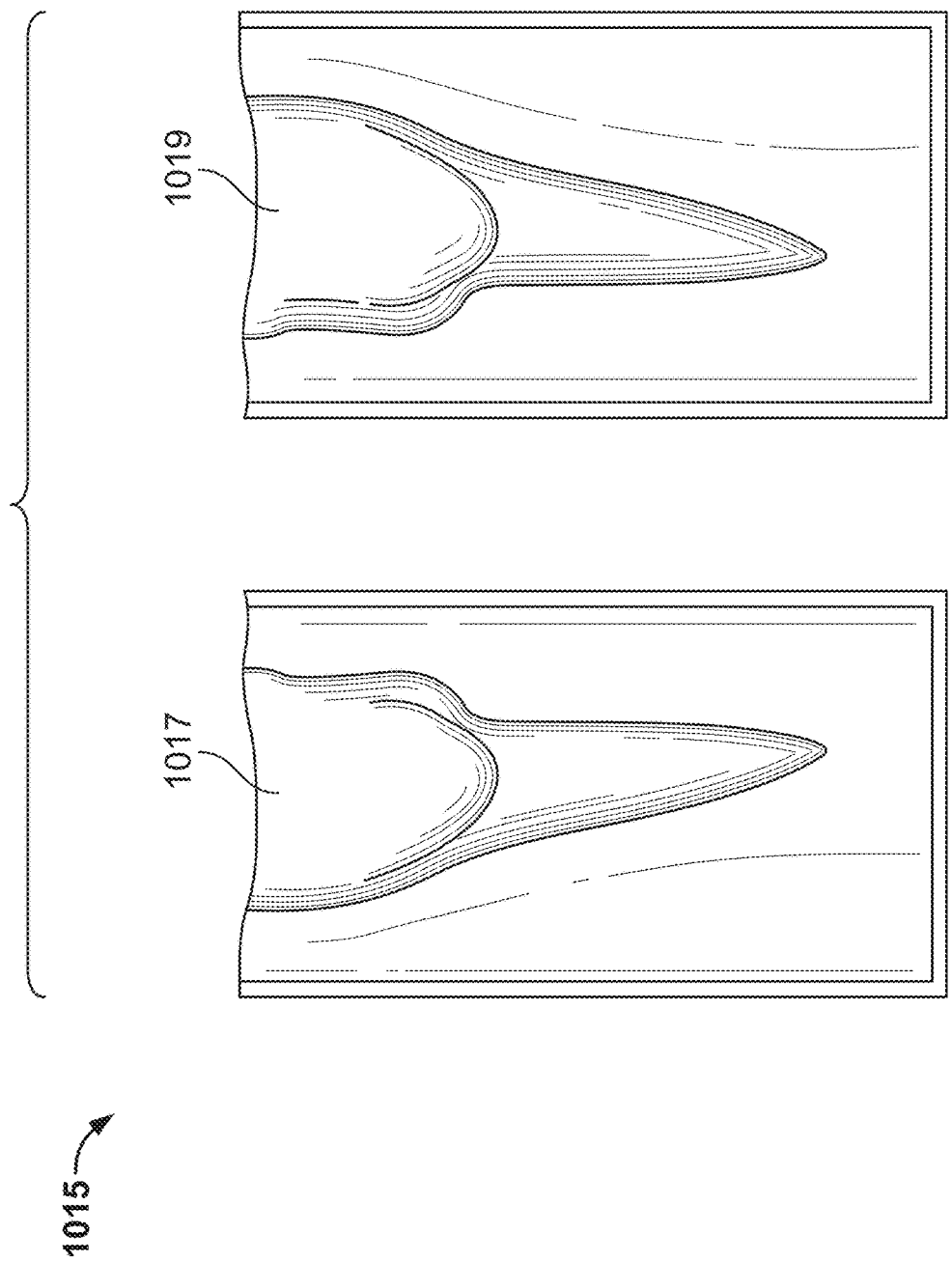
FIG. 17 is a view of silicone impression molds according to exemplary embodiments of the present disclosure.
Figure 18:
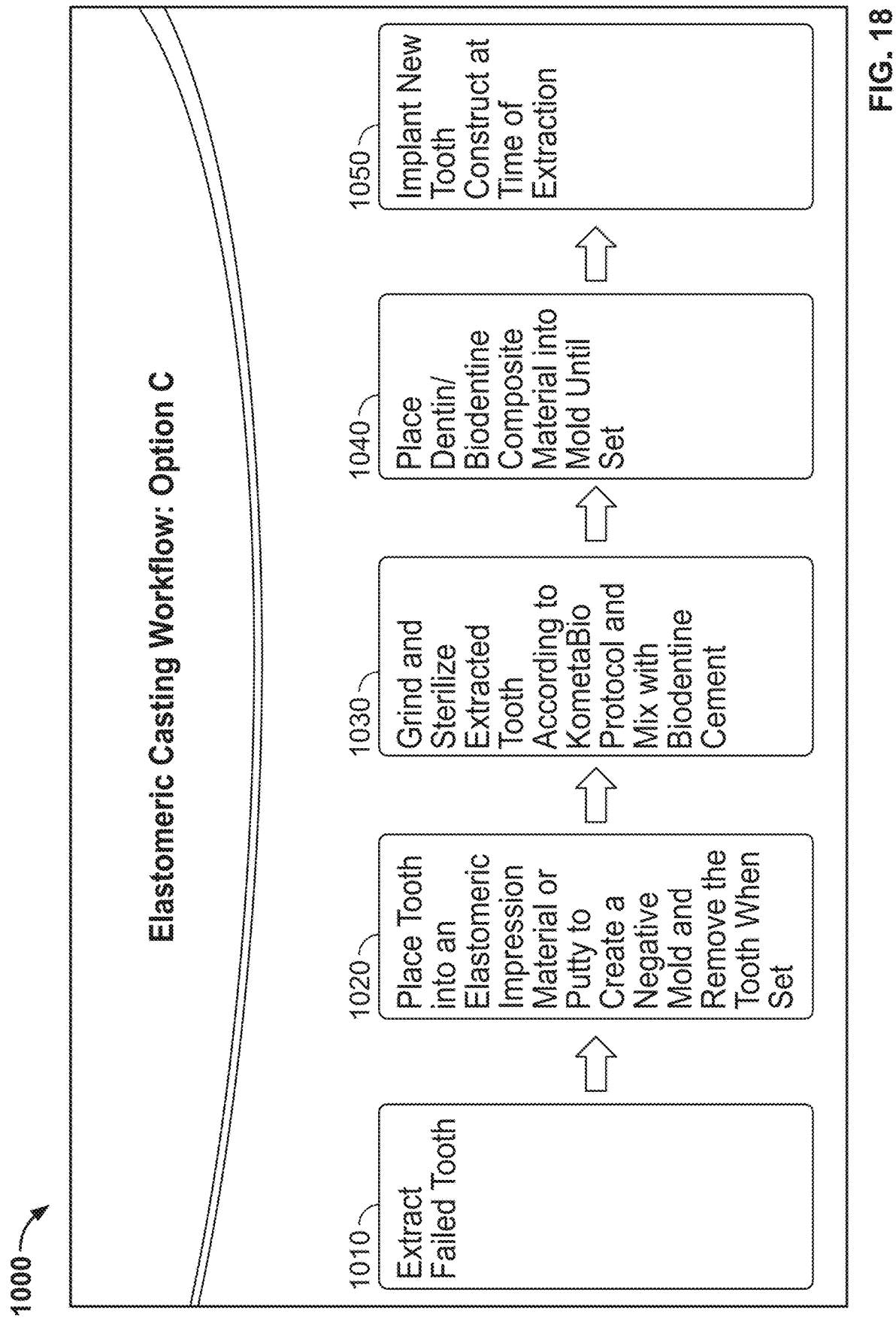
FIG. 18 is a flowchart setting forth the steps of an elastomeric casting process used to form a customized tooth form implant according to exemplary embodiments of the present disclosure.

FIGS. 17 and 18 illustrate one exemplary process for manufacturing a customized tooth form implant in accordance with the present invention and more particularly, an elastomeric casting process can be used as part of the manufacturing method.

FIG. 18 is a flowchart showing exemplary steps involved with a third method 1000 for manufacturing a customized tooth form implant.

The third method 1000 includes a first step 1010 of extracting the failed tooth. In a second step 1020, the extracted tooth is placed into an elastomeric impression material or putty to create a negative mold 1015, shown in FIG. 17, and then the extracted tooth is removed when impression material (putty) is set. FIG. 17 shows the mold 1015 which can be formed of a first mold cavity (first mold half) 1017 and a second mold cavity (second mold half) 1019. In this process, the set impression material is sectioned into two pieces with a blade and the original tooth is removed. It is important to split the material as cleanly and evenly (down the long axis) of the tooth as possible. This should help to form two relatively uniform halves.

In a third step 1030, the composite material (dentin/Biodentine) is placed into the impression mold 1015 and in particular, is placed into the hollow space of the first mold cavity 1017 and is placed into the hollow space of the second mold cavity 1019. The composite material is then allowed to set to form the hardened, cast tooth form implant.

In a fourth step 1040, the custom tooth form implant is then implanted and as mentioned with respect to the previous embodiment, the implantation, at least in one embodiment, can be performed at the time of extraction. The potential applications of the present invention could be for use as a temporary (transitional) or long term dental implant to immediately replace extracted teeth and/or a novel biocompatible composite material used as a fixation device, bone void filler, or osseoinductive material in alveolar bone and tissue regeneration.

This technology can be applied to satisfy many unmet market needs in the field of dental implantology. The present method and composite material would allow for a safer and more affordable procedure that can be performed by more providers to a wider range of patient populations. It has potential applications as an immediate implant in multiple age groups (especially patients between the ages of 6-21 years of age), numerous clinical scenarios, and can be commercialized globally due to the nature and availability of the materials, rapid chairside fabrication methods, and the relatively inexpensive cost of materials, equipment, and training.

This technology involves the use of a composite material composed of a person's (e.g., a patient's) processed tooth material being combined with a commercially available bioactive and biocompatible cement material in order to fabricate customizable patient specific tooth implants to immediately replace failing teeth.

Alternative Implant Fabrication

Figure 19:
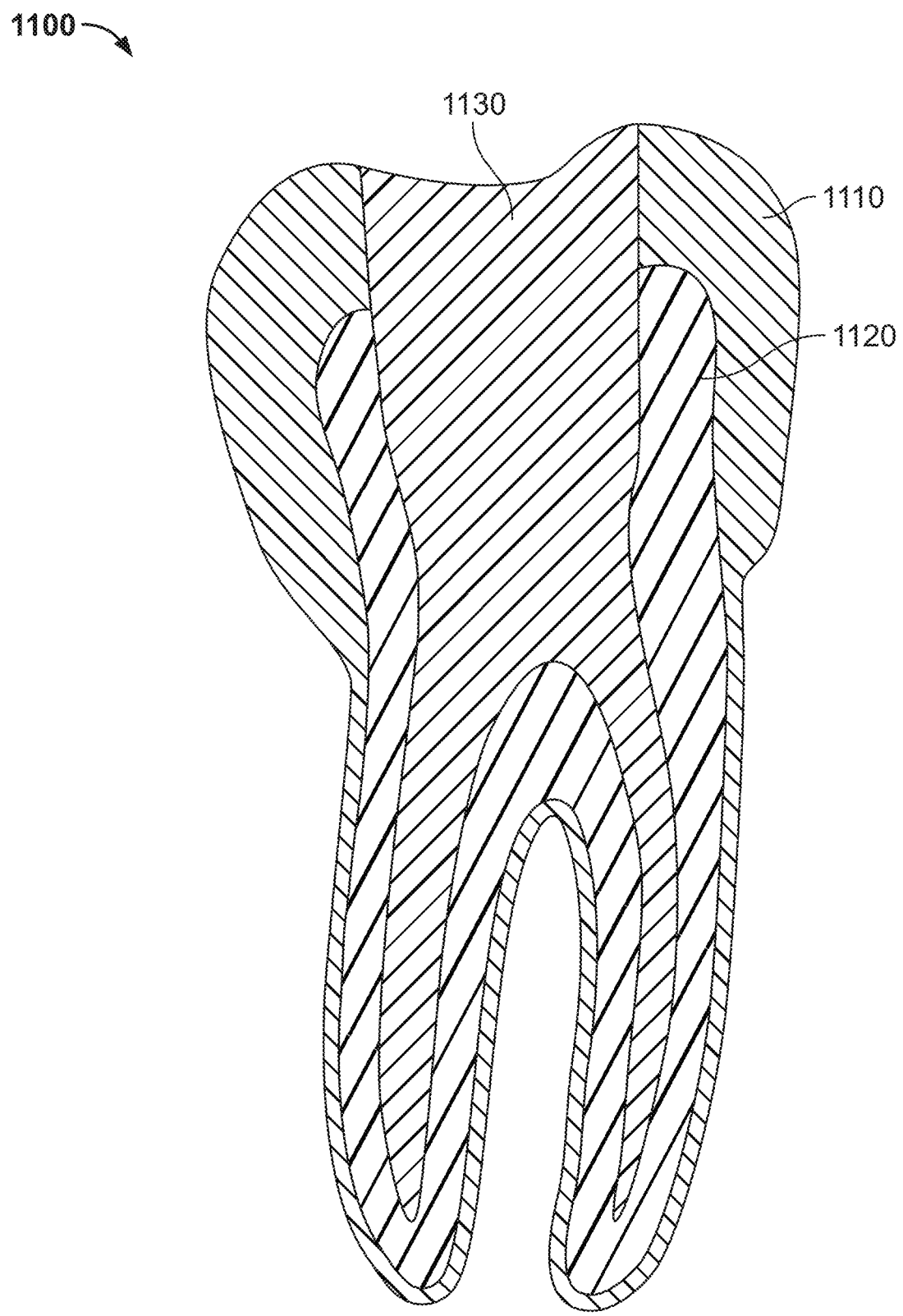
FIG. 19 is a cross-sectional view of another tooth form implant that is formed of an outer hollow shell formed from a patient's extracted tooth according to exemplary embodiments of the present disclosure.

In yet another alternative fabrication method that is illustrated in FIG. 19, a tooth implant 1100 is shown. The tooth implant 1100 fabrication process begins with the extraction of the tooth of the patient and then the internal aspect (discussed herein as being the core) of the patient's extracted tooth can be grinded away and a sterilization protocol discussed herein is followed (e.g., the sterilization protocol discussed herein with respect to the residual shell can be used) to sterile the tooth which is now in the form of a hollow tooth shell. In one embodiment, as shown in FIG. 19, the shell can be formed of the outer enamel layer 1110 and the dentin layer 1120. This intermediate structure can be considered to be a shell since the tooth has been hollowed out and only an outer tooth structure remains with a center void being created in the extracted tooth.

It will also be understood that in another embodiment, after extraction, the tooth can be prepared as by removing the enamel portion of the tooth leaving a dentin shell (dentin layer 1120) to be processed. The shell can be processed so that a good coronal tooth structure remains intact in that the enamel layer is removed and the tooth shell is prepared for receiving a conventional crown, while also being hollow out to the tip of the root. It will also be understood that one or more sections of the coronal portion may need to be removed due to decay or trauma, etc.

This alternative fabrication method is followed instead of grinding the dentin into particulate form prior to chemical sterilization. Once the fabricated hollow tooth shell is sterilized and the tubules are patent and free of debris, a bioactive cement material (described herein) is extruded directly into the hollow interior of the shell and allowed to set, thereby forming a core 1130 of the tooth implant 1100. It will be seen that the prepared tooth has been drilled from the top down to create the hollow shell and therefore, one or more holes are formed along the top portion of the tooth (i.e., the hole extends through the dentin layer and enamel layer when present) and therefore, as shown in FIG. 19, a top surface of the core 1130 may be visible along top surface of the coronal portion of the tooth.

The bioactive cement flows into the dentinal tubules thus creating another composite dentin/cement zone around the cement core 1130. The result is a fabricated implant 1100 similar to the ones described herein. The combined shell and core 1130 thus define the tooth implant that can be implemented into a site at which a tooth has been extracted.

It will also be understood that in the event that the enamel layer has been removed, a fabricated over layer for placement over the dentin layer may be contemplated and used (e.g., an outer layer such as the ones described herein).

In addition, the use of lasers, such as an Nd:YAG laser (e.g., PerioLase MVP07 from Millenium Dental Technologies), can be used with a variety of settings (ablation, biostimulation, etc.) directly into the extraction socket of the patient or focused directly on the dentin shell itself (see above description). Laser exposure can assist in decontaminating the extraction socket or tooth construct and also can help to promote periodontal regeneration by adjustment of the setting of the laser used (e.g., wavelength, duration, frequency of pulsed doses, and angulation of the laser to create specific surface patterning).

Shape of the Tooth Form Implant

It will be appreciated that the shape and construction of the new tooth form implant can be modified slightly in order to improve the path of insertion or increase its stability in the extraction socket. This is particularly useful for teeth with multiple roots or irregular curvatures. For example, a tooth that originally had three roots could be replaced by a two-rooted implant assuming the implant remains stable in the socket or a tooth with a curve at the apex (root tip) could be designed with a decreased curvature; or an extraction socket that is irregular due to bone loss or trauma could be stabilized by altering the shape of the implant (in CAD) to fill the irregular void.

Surface Modification of Implant

In yet another aspect of the present invention, surface modification can be performed on the implant (and/or the implant site as discussed below) at the time of implant placement (to promote periodontal regeneration/healing as well as to obtain other benefits).

There are a number of different types of surface modifications that can be performed at this time. For example, such surface modifications include the use of commercially available dental products applied to the implant construct surface (or the extraction socket) to promote periodontal healing. Thus, in one embodiment, a portion or the entire surface of the formed implant (e.g., one of the ones disclosed herein) can be modified. Applicant contemplates an improvement in terms of proliferation and viability of pertinent cell types responsible for periodontal regeneration when certain suitable biologic agents are supplemented at the implant/bone interface. Some of these products/biologies include Emdogain (EMD), Gem21s (PDGF), Bone morphogenic proteins (BMP), Amniospark (amnion growth factor liquid), autologous Platelet rich plasma (PRP) and/or Platelet rich fibrin (PRF) that when applied, may have an effect on pertinent cell types in direct contact with the implant surface.

In addition, polymeric delivery systems can be combined with these commonly used growth factors to control the release and enhance the efficacy of these surface modifications. Examples of these delivery systems can include newly developed biomaterials (i.e. hydrogels, polymeric films, nano or microspheres, and coatings) in combination with previously identified growth factors (i.e., Enamel matrix derivatives, PDGF, FGF or others mentioned above) on pertinent cell types in direct contact with the implant surface.

Compression Testing

Compression testing of these samples were conducted using an MTS (Sentech 5/D Model) mechanical tester using a 5000 lb. (approximately 23,000N) load cell at NJCBM. This is a slightly different model than what was used by Septodont, (the MTS Model 2/M, identified in the Biodentine Scientific File). In order to properly relate our findings to what was reported by Septodont, the present composite materials were tested against controls made of pure Biodentine cement. Typical compressive strength readings for the pure cement samples, measured as stress at yield, ranged between [115-137 MPa] (megapascals) and the amount of force applied, measured as load at yield, ranged from [10,151-11,679 N] (newtons). The most recent tests of our composite samples with the highest dentin composition (1:1 or 50% dentin particle to 50% cement powder) resulted in compressive strength ranging between [88-126 MPa] with a load at yield between [7031-10,315 N]. In comparison to human masticatory forces, the load applied during routine chewing has been typically reported in the literature between [80-300 N] with the highest bite forces recorded ranging between [300-900 N].

It will be understood that the composite implants described herein can have the capacity to form a new periodontal attachment during healing or ankylose. In other words, the composite implant may fuse directly to the jawbone.

Notably, the figures and examples above are not meant to limit the scope of the present invention to a single embodiment, as other embodiments are possible by way of interchange of some or all of the described or illustrated elements. Moreover, where certain elements of the present invention can be partially or fully implemented using known components, only those portions of such known components that are necessary for an understanding of the present invention are described, and detailed descriptions of other portions of such known components are omitted so as not to obscure the invention. In the present specification, an embodiment showing a singular component should not necessarily be limited to other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

The foregoing description of the specific embodiments will so fully reveal the general nature of the invention that others can, by applying knowledge within the skill of the relevant art(s) (including the contents of the documents cited and incorporated by reference herein), readily modify and/or adapt for various applications such specific embodiments, without undue experimentation, without departing from the general concept of the present invention. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

While various embodiments of the present disclosure have been described above, it should by understood that the embodiments have been presented by way of example, and not limitation. Thus, various changes in form and detail could be made therein without departing from the spirit and scope of the disclosure. Accordingly, the present invention should not be limited by any of the above-described exemplary embodiments, but should be defined only in accordance with the following claims and their equivalents.

What is claimed is:

1. A dental implant, comprising:
   a body comprising a biomimetic composite material,
      wherein the biomimetic composite material comprises processed dentin from an extracted tooth and a bioactive cement.

2. The dental implant of claim 1, wherein the processed dentin comprises dentin particles.

3. The dental implant of claim 1, wherein the bioactive cement comprises a calcium silicate based dental cement.

4. The dental implant of claim 1, wherein the body is formed entirely of the biomimetic composite material.

5. The dental implant of claim 1, wherein the body comprises a core and an outer surface layer that is disposed over at least a portion of the core.

6. The dental implant of claim 5, wherein the core is formed at least substantially of the bioactive cement and the outer surface layer is formed of the biomimetic composite material.

7. The dental implant of claim 6, wherein a thickness of the outer surface layer is between about 500 microns and about 1500 microns.

8. The dental implant of claim 6, wherein the outer surface layer covers at least substantially all of the core.

9. The dental implant of claim 6, wherein the dentin comprises from about 10 percent to about 50 percent by weight of the total biomimetic composite material.

10. The dental implant of claim 1, wherein the dentin comprises from about 10 percent to about 50 percent by weight of the total biomimetic composite material.

11. The dental implant of claim 1, wherein the biomimetic composite material comprises dentin particles, in powder form, mixed with the bioactive cement.

12. The dental implant of claim 2, wherein the dentin particles have a particle size between about 50 microns and about 1500 microns.

13. The dental implant of claim 1, wherein the dentin comprises a plurality of dentin particles with each particle have a multitude of exposed dentinal tubules, the biomimetic composite material being defined by micro-mechanical bonding of the bioactive cement to the dentin particles as a result of flow of the bioactive cement into the dentinal tubules.

14. The dental implant of claim 1, wherein a final shape and size of the body are selected in view of an image of the tooth that is extracted and mimics the shape and size of the extracted tooth.

15. The dental implant of claim 1, wherein the bioactive cement comprises a dental cement selected from the group consisting of: a calcium silicate-based cement, a mineral trioxide aggregate (MTA), and a glass ionomer cement.

* * * * *

UNITED STATES PATENT AND TRADEMARK OFFICE
CERTIFICATE OF CORRECTION

| | | |
|---|---|---|
| PATENT NO. | : 11,406,478 B2 | Page 1 of 1 |
| APPLICATION NO. | : 16/791090 | |
| DATED | : August 9, 2022 | |
| INVENTOR(S) | : Amir Fakhrzadeh et al. | |

It is certified that error appears in the above-identified patent and that said Letters Patent is hereby corrected as shown below:

In the Specification

Column 1, starting at Line 23 insert:
--STATEMENT REGARDING FEDERALLY SPONSORED RESEARCH OR DEVELOPMENT
This invention was made with government support under grant number EB005583 awarded by the National Institutes of Health. The government has certain rights in the invention.--

Signed and Sealed this
Twelfth Day of September, 2023

Katherine Kelly Vidal
*Director of the United States Patent and Trademark Office*